(12) United States Patent
Ulrich et al.

(10) Patent No.: US 7,291,654 B2
(45) Date of Patent: Nov. 6, 2007

(54) STORAGE STABILITY OF PHOTOINITIATORS

(75) Inventors: Thomas Ulrich, Olten (CH); Thomas Bolle, Efringen-Kirchen (DE); Kurt Dietliker, Allschwil (CH); Jean-Pierre Wolf, Maisprach (CH); André Fuchs, Schliengen-Obereggenen (DE)

(73) Assignee: Ciba Specialty Chemicals Corporation, Tarrytown, NY (US)

( * ) Notice: Subject to any disclaimer, the term of this patent is extended or adjusted under 35 U.S.C. 154(b) by 412 days.

(21) Appl. No.: 10/531,482

(22) PCT Filed: Oct. 17, 2003

(86) PCT No.: PCT/EP03/50729

§ 371 (c)(1),
(2), (4) Date: Apr. 15, 2005

(87) PCT Pub. No.: WO2004/037799

PCT Pub. Date: May 6, 2004

(65) Prior Publication Data

US 2006/0100298 A1    May 11, 2006

(30) Foreign Application Priority Data

Oct. 28, 2002   (CH) ..................... 1800/02

(51) Int. Cl.
C07D 295/10 (2006.01)
C07D 295/12 (2006.01)
C08F 2/46 (2006.01)
C09D 11/10 (2006.01)
G03F 7/028 (2006.01)

(52) U.S. Cl. ............... 522/8; 522/21; 522/39; 544/175; 568/308

(58) Field of Classification Search ............ 522/8, 522/9, 10, 39, 42
See application file for complete search history.

(56) References Cited

U.S. PATENT DOCUMENTS

| | | | |
|---|---|---|---|
| 5,077,402 A | 12/1991 | Desobry et al. | 544/87 |
| 5,532,112 A * | 7/1996 | Kohler et al. | 430/281.1 |
| 5,534,629 A | 7/1996 | Desobry et al. | 544/78 |
| 5,629,356 A | 5/1997 | Desobry et al. | 522/34 |
| 6,140,326 A * | 10/2000 | Lazzari et al. | 514/231.2 |
| 6,191,182 B1 | 2/2001 | Husler et al. | 522/39 |
| 6,228,289 B1 * | 5/2001 | Powers et al. | 264/1.36 |
| 6,344,299 B1 * | 2/2002 | Sato et al. | 430/7 |
| 6,579,913 B2 * | 6/2003 | Klinkenberg et al. | 522/14 |
| 6,620,857 B2 * | 9/2003 | Valet | 522/42 |
| 7,071,255 B2 * | 7/2006 | Nishimura et al. | 524/430 |
| 7,173,071 B2 * | 2/2007 | Suhadolnik et al. | 522/18 |

* cited by examiner

*Primary Examiner*—Susan W Berman
(74) *Attorney, Agent, or Firm*—Shiela A. Loggins

(57) ABSTRACT

Compounds of formula (I), wherein $R_1$ is hydrogen or alkyl; $R_2$ is $C_1$-$C_4$alkoxy or a morpholino radical; and $R_3$ is hydrogen or $C_1$-$C_4$alkoxy, are suitable for improving the solubility of specific photoinitiators in formulations and accordingly enhance the storage stability of formulations comprising a photoinitiator and compounds of formula (I)

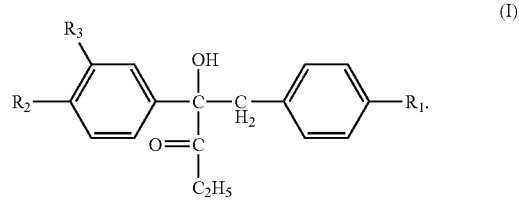

(I)

15 Claims, No Drawings

STORAGE STABILITY OF PHOTOINITIATORS

The invention relates to specific compounds suitable for improving the storage stability of formulations comprising selected photoinitiators, to mixtures of such compounds with the photoinitiators being stabilised and to corresponding photocurable compositions.

The use of certain ketone compounds, especially α-aminoketones, as photoinitiators is known in the art and is described, for example, in U.S. Pat. No. 5,077,402, U.S. Pat. No. 5,534,629 and U.S. Pat. No. 5,629,356. U.S. Pat. No. 6,191,182 discloses a special preparation process for such compounds.

When the photoinitiators are dissolved in formulations, the formulations often have to be used immediately, because storage-stability problems, for example caused by crystallisation of the initiator, may occur. It has now been found that certain photoinitiators in formulations exhibit improved storage stability when the initiators are mixed with specific compounds.

The invention accordingly relates to compounds of formula (I)

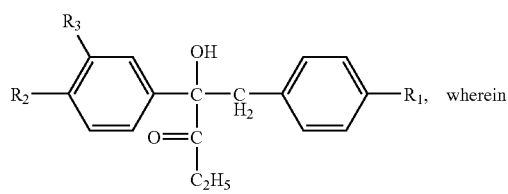

(I)

wherein $R_1$ is hydrogen or alkyl;
$R_2$ is $C_1$-$C_4$alkoxy or a morpholino radical; and
$R_3$ is hydrogen or $C_1$-$C_4$alkoxy.

The addition of such compounds to formulations that comprise certain α-aminoketone photoinitiator compounds brings about an improvement in the storage stability of those formulations.

"Alkyl" is linear or branched and is, for example, $C_1$-$C_{12}$-, $C_1$-$C_8$-, $C_1$-$C_6$- or $C_1$-$C_4$-alkyl. Examples are methyl, ethyl, propyl, isopropyl, n-butyl, sec-butyl, isobutyl, tert-butyl, pentyl, hexyl, heptyl, 2,4,4-trimethyl-pentyl, 2-ethylhexyl, octyl, nonyl, decyl, undecyl, dodecyl. $R_1$ is, for example, $C_1$-$C_8$alkyl, especially $C_1$-$C_6$alkyl, preferably $C_1$-$C_4$alkyl, e.g methyl or butyl, preferably methyl.

"$C_1$-$C_4$Alkoxy" denotes linear or branched radicals and is, for example, methoxy, ethoxy, propoxy, isopropoxy, n-butoxy, sec-butoxy, isobutoxy or tert-butoxy, preferably methoxy.

The term "morpholino radical" denotes the following group:

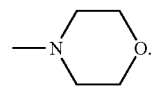

The term "and/or" is intended to indicate that not only one of the defined alternatives (substituents) may be present but several different defined alternatives (substituents) may be present together, that is to say mixtures of different alternatives (substituents) may be present.

The term "at least one" is intended to indicate "one or more than one", e.g. one or two or three, preferably one or two.

The word "comprising" in the description and the patent claims is to be understood as including a defined subject or a defined group of subjects, but without excluding any other substances not specifically mentioned, unless expressly described to the contrary.

1. Compounds of the formula (I) can for example be prepared by Grignard reaction of a suitable benzyl-Grignard reagent with a corresponding diketone compound. Nucleophilic substitution of the fluoro group in 4'-fluoro-1-phenyl-butane-1,2-dione with morpholine as for example described in U.S. Pat. No. 6,191,182 renders 4'-morpholino-1-phenyl-butane-1,2-dione. The following Grignard reaction with an (optionally substituted) benzyl magnesium bromide (benzyl magnesium chloride, benzyl magnesium iodide) followed by column chromatography as described by Miyashita in Chem. Pharm. Bull.; 46 (1), 1998, p. 6-11, or by Holm in Acta Chem. Scand. Ser. B; 41(4),1987, p. 278-284 gives the desired product.

$R_1$ is defined as described above.

The Grignard reagent can for example be replaced by a corresponding benzyl trimethyl stannane derivative as the reagent in an acid-mediated or photochemical addition reaction as described by Takuwa, Chem. Lett.; 4, 1990, p. 639-642.

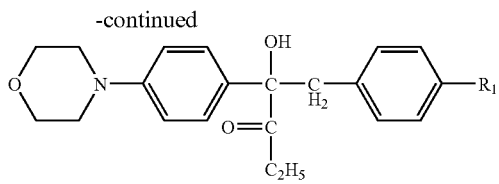

$R_1$ is defined as described above.

Compounds of the formula (I) wherein $R_2$ and $R_3$ are $C_1$-$C_4$alkoxy are prepared in a similar manner, starting from 3',4'-dialkoxy-1-phenyl-butane-1,2-dione, e.g. 3',4'-dimethoxy-1-phenyl-butane-1,2-dione, by Grignard reaction with a corresponding benzyl magnesium bromide (benzyl magnesium chloride, benzyl magnesium iodide) or by an acid-mediated or photochemical addition reaction with benzyl trimethyl stannane:

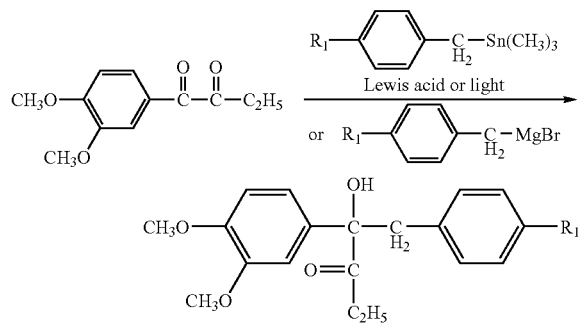

$R_1$ is defined as described above.

2. Starting from 1-hydroxy-1-(4-morpholinophenyl)-butan-2-one or 1-hydroxy-1-(3,4-dimethoxyphenyl)-butan-2-one, compounds of the formula (I) are obtained by alkylation with a corresponding, optionally substituted, benzyl bromide (benzyl chloride, benzyl iodide) under basic conditions in a polar solvent like for example dimethyl sulfoxide (DMSO) as described by Miyashita in Chem. Pharm. Bull.; 46(1), 1998, p. 6-11 or by Heine in Justus Liebigs Ann. Chem.; 735,1970, p. 56-64:

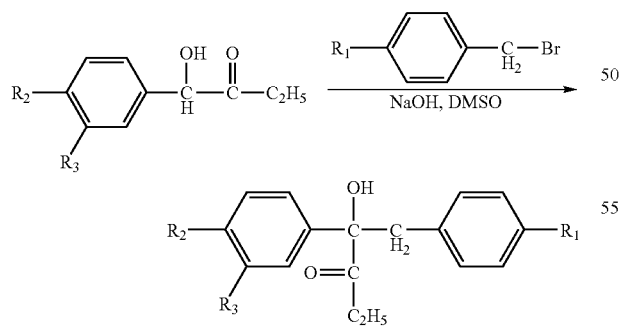

$R_1$, $R_2$ and $R_3$ are defined as described above.

3. Another way to prepare compounds of the formula (I) is the following: the silylated cyanohydrin of propanal is treated with lithium diisopropylamide (LDA) in tetrahydrofuran (THF) at low temperature The anion thus obtained adds to the carbonyl group of suitably substituted 1,2-diphenylethanone derivatives [1-(4-morpholinophenyl)-2-(4-methylphenyl)-ethanone for the synthesis of compounds of formula (I) wherein $R_2$ is a morpholino group and $R_1$ is methyl, 1-(4-morpholinophenyl)-2-phenyl-ethanone for the synthesis of compounds of formula (I) wherein $R_2$ is a morpholino group and $R_1$ is hydrogen or 1-(3,4-dimethoxyphenyl)-2-phenyl-ethanone for the synthesis of compounds of formula (I) wherein $R_2$ and $R_3$ are methoxy]. The primary adducts undergo an 1,4-O,O-silyl shift with loss of cyanide to give the silyl ethers of the corresponding compounds, which are then hydrolysed to the corresponding α-hydroxyketones. Instead of trimethylsilyl ethers, other silyl ethers such as tert-butyl-dimethyl-silyl ethers or hexyl-dimethyl-silyl ethers can be used as starting materials as well. Such reaction conditions are described e.g. in Hünig, S.; Wehner, G. Chem. Ber. 1979, 112, 2062; or Hünig, S., Marschner, C.; Chem. Ber. 1989, 122, 1329:

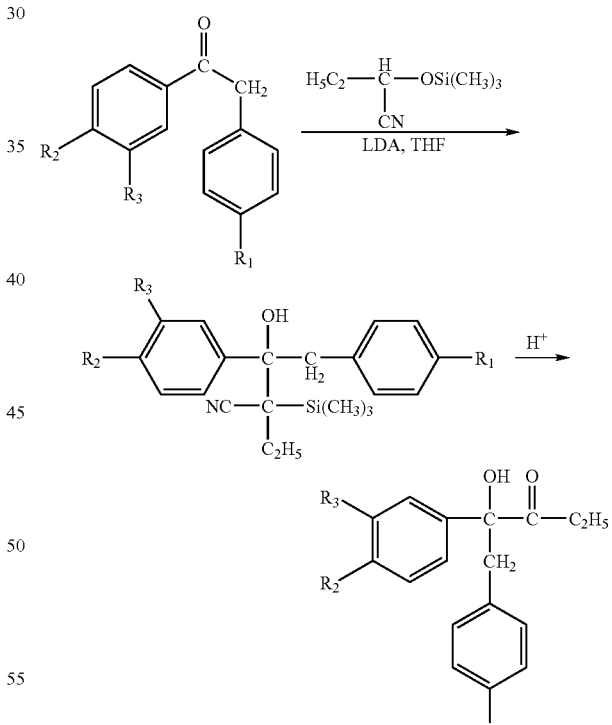

$R_1$, $R_2$ and $R_3$ are defined as described above.

4. Grignard reaction of ethylmagnesium bromide with the silylated cyanohydrins of suitably substituted 1,2-diphenylethanone derivatives produces the silyl ethers of the imines of compounds of formula (I). Acid-catalysed hydrolytic cleavage of the silyl ether and simultaneous hydrolysis of the imine gives the corresponding α-hydroxy ketones, as reported in Gill, M., Milton. J.; Deborah, A. Tetrahedron

*Lett.* 1986, 27, 1933; Murata, S. Yamabe, K., Tashiro, K.; Ishibashi, Y. *Chem. Express* 1988, 3, 363:

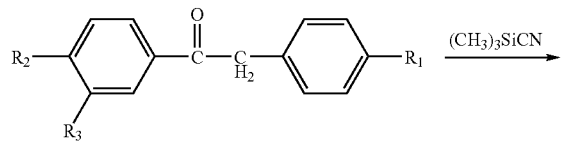

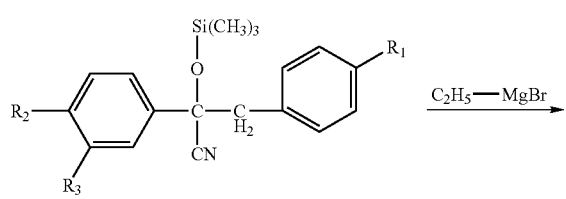

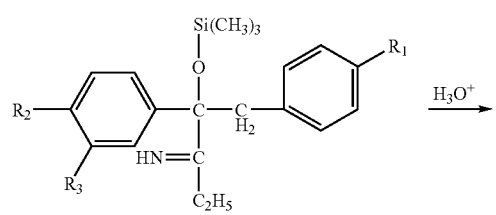

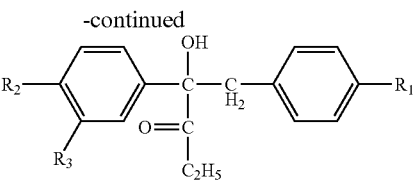

$R_1$, $R_2$ and $R_3$ are defined as described above.

5. Condensation of N-tosyl-glycinol with an excess of triethyl orthopropionate affords the 2-ethoxy-1,3-oxazolidine. This compound is transformed into the 2-cyano-1,3-oxazolidine by the trimethyltriflate-catalysed reaction with trimethylsilyl cyanide as reported by Harder, T.; Löhl, T.; Bolte, M.; Wagner, K.; Hoppe, D. *Tetrahedron Letters* 1994, 35, 7365. Addition of (optionally substituted) benzylmagnesium bromide to the nitrile after acid-catalysed hydrolysis of the imine yields the ketone, which is subsequently subjected to a second Grignard reaction using a suitably substituted arylmagnesium bromide such as 3,4-dimethoxyphenyl-magnesium bromide for the preparation of a compound of formula (I) wherein $R_2$ and $R_3$ are methoxy. The oxazolidine protective group is subsequently removed by electrochemical reductive detosylation, followed by hydrolysis of the intermediate 3H-substituted oxazolidine during aqueous work-up, providing the a-hydroxy ketone product as reported by Harder, T.; Löhl, T.; Bolte, M.; Wagner, K.; Hoppe, D. *Tetrahedron Letters* 1994, 35, 7365:

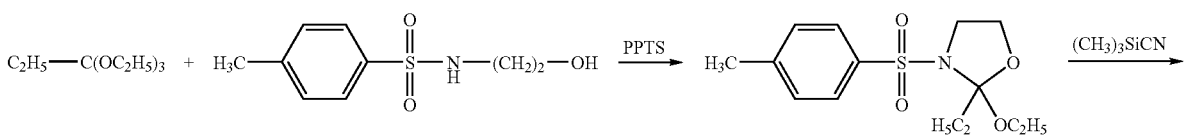

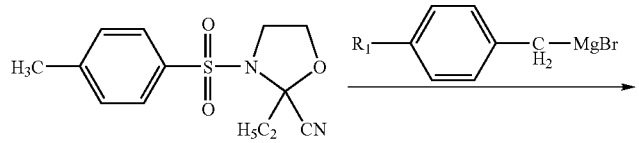

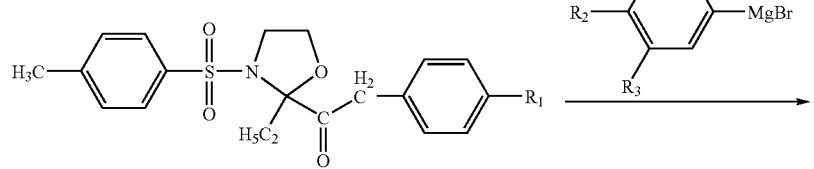

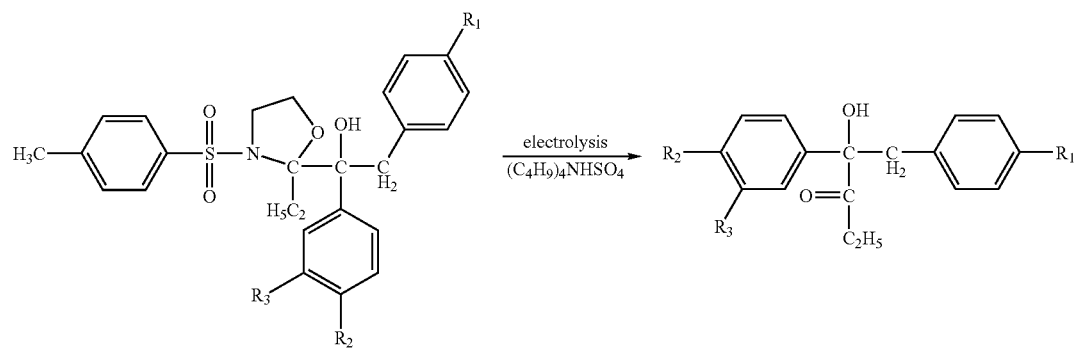

$R_1$, $R_2$ and $R_3$ are defined as described above. PPTS means pyridine tosylate.

The preparation of the starting materials for the above-mentioned methods for the synthesis of compounds of the formula (I) is known to the person skilled in the art and described in the literature.

(a) Diketones, such as 1-(4-fluorophenyl)-1-phenyl-butane-1,2-dione, 1-(4-morpholino-phenyl)-1-phenyl-butane-1,2-dione and 1-(3,4-dimethoxyphenyl)-1-phenyl-butane-1,2-dione and (b) hydroxy ketones, such as 1-hydroxy-1-(4-fluorophenyl)-butan-2-one, 1-hydroxy-1-(4-morpholinophenyl)-butan-2-one and 1-hydroxy-1-(3,4-dimethoxyphenyl)-butan-2-one.

Addition of ethyl magnesium iodide (ethyl magnesium bromide, ethyl magnesium chloride) to the cyanohydrin prepared from 4-fluoro-benzaldehyde, 4-morpholino-benzaldehyde or 3,4-dimethoxy-benzaldehyde according to Kaji, in Yakugaku Zasshi; 76, 1956, p. 1250 and 1253, renders 1-hydroxy-1-(4-fluorophenyl)-butan-2-one, 1-hydroxy-1-(4-morpholinophenyl)-butan-2-one and 1-hydroxy-1-(3,4-dimethoxyphenyl)-butan-2-one:

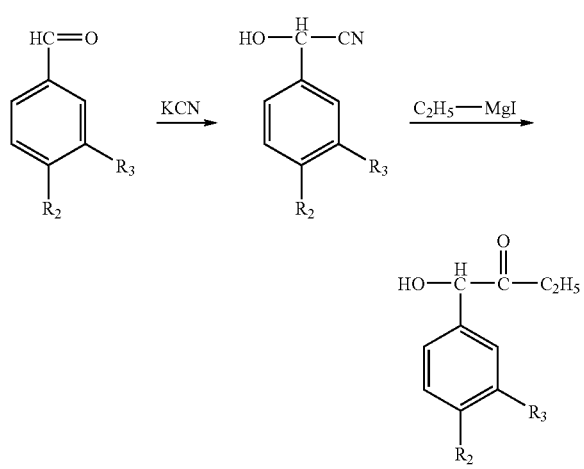

$R_1$, $R_2$ and $R_3$ are defined as above, wherein $R_2$ additionally can be F.

If desired, the Grignard reagent can also be added to the trimethylsilane-protected cyanohydrin of 4-fluoro-benzaldehyde, 4-morpholino-benzaldehyde or 3,4-dimethoxy-benzaldehyde as e.g. described in Gill, M.; Kiefel, M.; Lally, D. A. Tetrahedron Lett. 1986, 27.1933. The corresponding trimethylsilane-protected cyanohydrins are obtained by reacting 4-fluoro-benzaldehyde, 4-morpholino-benzaldehyde or 3,4-dimethoxy-benzaldehyde with trimethylsilyl cyanide and zinc iodide according to Schnur, J. Med. Chem.; 29(5), 1986, p. 770-778. Alternatively, the silyl-protected cyanohydrins can be prepared by the reaction of the corresponding benzaldehyde with trimethylchlorosilane and potassium cyanide in the presence of catalytic amounts of zinc cyanide as described in U.S. Pat. No. 4,524,221. Instead of trimethylsilyl derivatives, other silyl compounds such as tert-butyl-dimethylsilyl or thexyldimethylsilyl derivatives can be used as well.

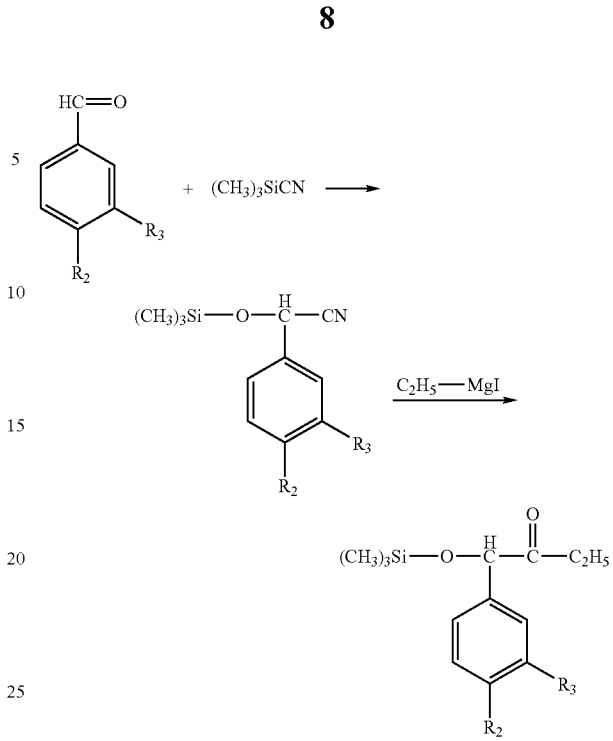

The trimethylsilyl group can be removed by treatment with aqueous acid according to Schnur, J. Med. Chem.; 29(5)) 1986, p. 770-778.

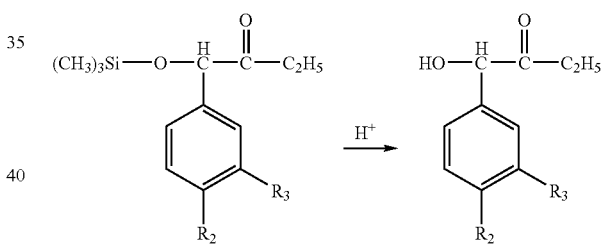

Oxidation of 1-hydroxy-1-(4-fluorophenyl)-butan-2-one, 1-hydroxy-1-(4-morpholinophenyl)-butan-2-one and 1-hydroxy-1-(3,4-dimethoxyphenyl)-butan-2-one with manganese dioxide according to Adler, Acta. Chem. Scand.; 15, 1961, p. 849-852 gives the corresponding diketones 1-(4-fluorophenyl)-1-phenyl-butane-1,2-dione, 1-(4-morpholinophenyl)-1-phenyl-butane-1,2-dione and 1-(3,4-dimethoxyphenyl)-1-phenyl-butane-1,2-dione.

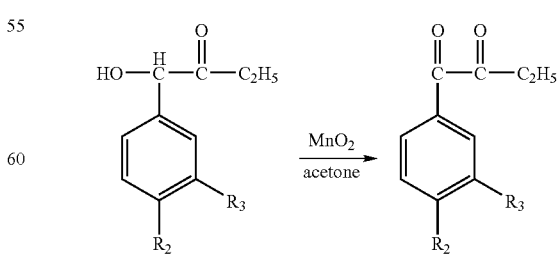

1-(3,4-Dimethoxyphenyl)1-phenyl-butane-1,2-dione can for example alternatively also be prepared from orthodimethoxy-benzene and 2-oxo-butyronitrile with HCl in diethyl ether as described by Borsche in Chem. Ber.; 63, 1930, p. 2740 and 2742.

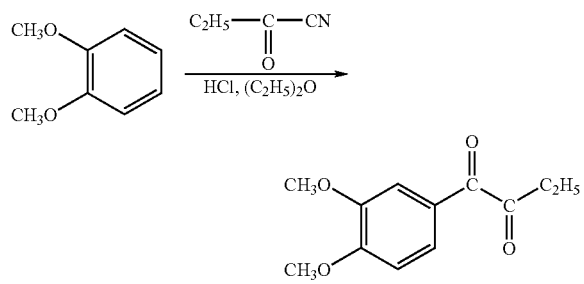

An additional method to prepare 1-hydroxy-1-(4-fluorophenyl)-butan-1-one, 1-hydroxy-1-(4-morpholinophenyl)-butan-1-one and 1-hydroxy-1(3,4-dimethoxyphenyl)-butan-1-one is given by the reaction of 4-fluoro-benzoic acid ethyl ester, 4-morpholino-benzoic acid ethyl ester and 3,4-dimethoxy-benzoic acid ethyl ester with propionic acid ethyl ester using sodium in xylene as described by Lynn in J. Amer. Chem. Soc.; 73, 1951, p. 4284.

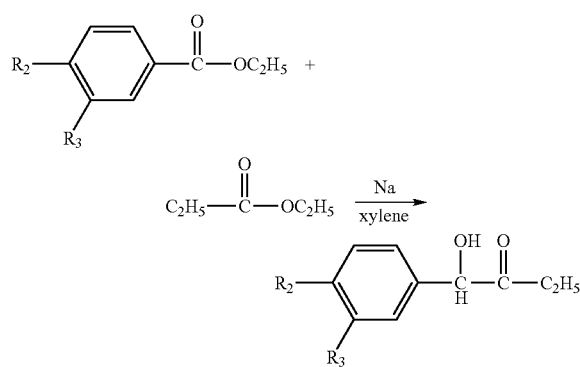

The corresponding diketones are obtained by oxidation with e.g. manganese dioxide as described above.

(c) Benzyl phenyl ketones such as benzyl 3,4-dimethoxyphenyl ketone, benzyl 4-morpholinophenyl ketone and 4-methylbenzyl 4-morpholinophenyl ketone.

Starting from 4-fluoro-benzamide, 4-morpholino-benzamide or 3,4-dimethoxy-benzamide, the corresponding benzyl phenyl ketones can be made by reaction with the Grignard reagent benzyl magnesium bromide (benzyl magnesium chloride, benzyl magnesium iodide), 4-methyl benzyl magnesium bromide (4-methyl benzyl magnesium chloride, 4-methyl benzyl magnesium iodide) as described for example by Tiffeneau in Bull. Chem. Soc.; 37, 1925, p. 1250.

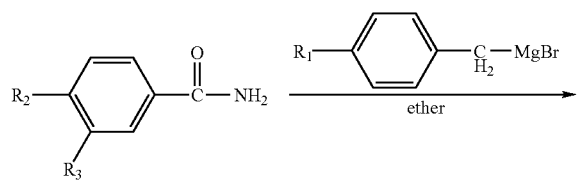

-continued

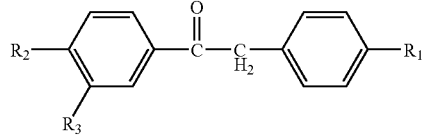

Alternatively, the same products can be made by addition of the above-mentioned Grignard reagents to the benzaldehydes as described above followed by oxidation of the alcohol to the ketone with manganese dioxide as for example described by Adler in Acta. Chem. Scand.; 15, 1961, p. 849-852.

The synthesis of 1-(4-morpholinophenyl)-2-phenyl-ethanone has been reported in Schneider, M. R.; Schuderer, M. L. Arch. Pharm. 1989, 322, 59, that of 1-(3,4-dimethoxyphenyl)-2-phenyl-ethanone in Dyke, S. F.; Tiley, E. P.; White, A. W. C.; Gale, D. P. Tetrahedron (1975), 31(9), 1219-22.

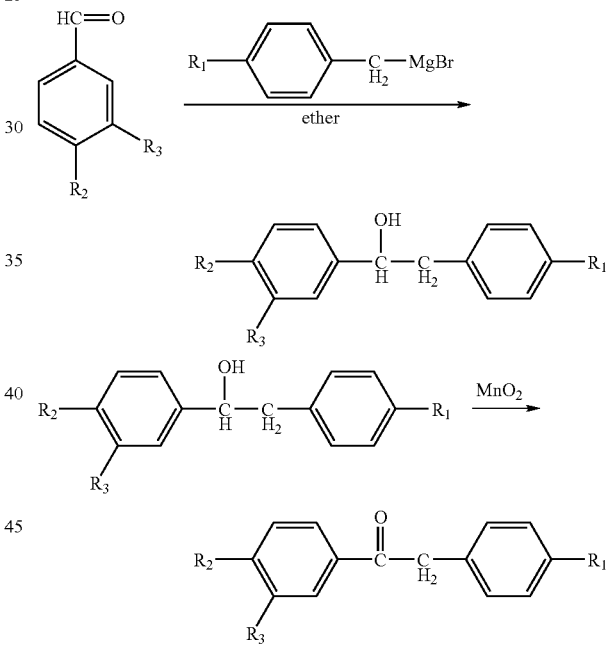

Preference is given to compounds of formula (I) wherein
$R_1$ is hydrogen or $C_1$-$C_4$alkyl, especially methyl;
$R_2$ is methoxy or a morpholino radical; and
$R_3$ is hydrogen or methoxy.

Special mention should be made of the following compounds of formula (I)

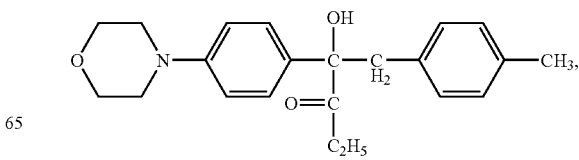

-continued

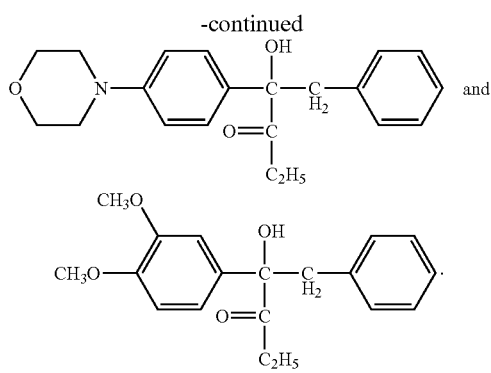

and

As already mentioned, the addition of compounds of formula (I) to certain photoinitiators increases the solubility of the latter in formulations and therefore increases the storage stability of those formulations.

The invention therefore relates to the use of compounds of formula (I) as storage-stability improvers for formulations comprising compounds of formula (II) as defined hereinbelow; and to a method of improving the storage stability of formulations comprising compounds of formula (II) as defined hereinbelow, wherein at least one compound of formula (I) as defined above is added to those formulations.

Also of interest, therefore, are mixtures of the compounds of formula (I) with photoinitiators. The invention relates especially to mixtures of compounds of formula (I), as defined above, with compounds of formula (II)

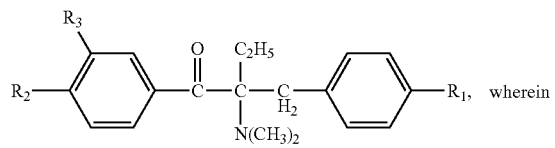 wherein $R_1$, $R_2$ and $R_3$ are as defined above.

Preference is given to mixtures of compounds of formulae (I) and (II) wherein the radicals $R_1$, $R_2$ and $R_3$ each have the same meanings for both structures.

Preferred mixtures of compounds of formula (I) with compounds of formula (II) comprise compounds of formula (I) and compounds of formula (II) wherein in each case $R_1$ is methyl, $R_2$ is a morpholino radical and $R_3$ is hydrogen; or comprise compounds of formula (I) and compounds of formula (II) wherein in each case $R_1$ is hydrogen, $R_2$ is a morpholino radical and $R_3$ is hydrogen;
or comprise compounds of formula (I) and compounds of formula (II) wherein in each case $R_1$ is hydrogen and $R_2$ and $R_3$ are methoxy.

The mixtures according to the invention of compounds of formula (I) with compounds of formula (II) contain from 0.1 to 10% compounds of formula (I) and from 90 to 99.9% compounds of formula (II), e.g. from 0.2 to 8% compounds of formula (I) and from 92 to 99.8% compounds of formula (II), preferably from 0.3 to 4% compounds of formula (I) and from 96 to 99.7% compounds of formula (II).

The compounds of formula (II) are photoinitiators. The addition of compounds of formula (I) to formulations comprising those photoinitiators surprisingly does not have any adverse effect on the properties of those photoinitiators. That is to say, both the reactivity and the yellowing properties of the initiators remain unchanged.

The invention relates also to photopolymerisable compositions, comprising
(A) at least one ethylenically unsaturated photopolymerisable compound,
(B) at least one photoinitiator compound of formula (II) as defined above, and
(C) as storage-stability improver at least one compound of formula (I) as defined above; it being possible for the composition to comprise, in addition to component (B), other photoinitiators (E) and/or other additives (D).

The unsaturated compounds (A) may contain one or more olefinic double bonds. They may be low molecular weight (monomeric) or higher molecular weight (oligomeric). Examples of monomers having a double bond are alkyl and hydroxyalkyl acrylates and methacrylates, e.g. methyl, ethyl, butyl, 2-ethylhexyl and 2-hydroxyethyl acrylate, isobornyl acrylate and methyl and ethyl methacrylate. Also of interest are resins modified with silicon or fluorine, e.g. silicone acrylates. Further examples are acrylonitrile, acrylamide, methacrylamide, N-substituted (meth)acrylamides, vinyl esters, such as vinyl acetate, vinyl ethers, such as isobutyl vinyl ether, styrene, alkyl- and halo-styrenes, N-vinylpyrrolidone, vinyl chloride and vinylidene chloride.

Examples of monomers having a plurality of double bonds are ethylene glycol diacrylate, 1,6-hexanediol diacrylate, propylene glycol diacrylate, dipropylene glycol diacrylate, tripropylene glycol diacrylate, neopentyl glycol diacrylate, hexamethylene glycol diacrylate and bisphenol A diacrylate, 4,4'-bis(2-acryloyloxyethoxy)diphenylpropane, trimethylolpropane triacrylate, pentaerythritol triacrylate and pentaerythritol tetraacrylate, vinyl acrylate, divinylbenzene, divinyl succinate, diallyl phthalate, triallyl phosphate, triallyl isocyanurate, tris(hydroxyethyl)isocyanurate triacrylate and tris(2-acryloylethyl)isocyanurate.

It is also possible in radiation-curable systems to use acrylic esters of alkoxylated polyols, for example glycerol ethoxylate triacrylate, glycerol propoxylate triacrylate, trimethylolpropane ethoxylate triacrylate, trimethylolpropane propoxylate triacrylate, pentaerythritol ethoxylate tetraacrylate, pentaerythritol propoxylate triacrylate, pentaerythritol propoxylate tetraacrylate, neopentyl glycol ethoxylate diacrylate or neopentyl glycol propoxylate diacrylate. The degree of alkoxylation of the polyols used may vary.

Examples of higher molecular weight (oligomeric) polyunsaturated compounds are acrylated epoxy resins, acrylated or vinyl-ether- or epoxy-group-containing polyesters, polyurethanes and polyethers. Further examples of unsaturated oligomers are unsaturated polyester resins, which are usually produced from maleic acid, phthalic acid and one or more diols and have molecular weights of about from 500 to 3000. In addition it is also possible to use vinyl ether monomers and oligomers, and also maleate-terminated oligomers having polyester, polyurethane, polyether, polyvinyl ether and epoxide main chains. Combinations of vinyl-ether-group-carrying oligomers and polymers, as described in WO 90/01512, are especially suitable, but copolymers of monomers functionalised with maleic acid and vinyl ether also come into consideration. Such unsaturated oligomers can also be termed prepolymers.

Especially suitable are, for example, esters of ethylenically unsaturated carboxylic acids and polyols or polyepoxides, and polymers having ethylenically unsaturated groups in the chain or in side groups, e.g. unsaturated polyesters, polyamides and polyurethanes and copolymers thereof, alkyd resins, polybutadiene and butadiene copolymers, polyisoprene and isoprene copolymers, polymers and copolymers having (meth)acrylic groups in side chains, and also mixtures of one or more such polymers.

Examples of unsaturated carboxylic acids are acrylic acid, methacrylic acid, crotonic acid, itaconic acid, cinnamic acid and unsaturated fatty acids, such as linolenic acid and oleic acid. Acrylic and methacrylic acid are preferred.

Suitable polyols are aromatic and especially aliphatic and cycloaliphatic polyols. Examples of aromatic polyols are hydroquinone, 4,4'-dihydroxydiphenyl, 2,2-di(4-hydroxyphenyl)propane, and novolaks and resols. Examples of polyepoxides are those based on the said polyols, especially the aromatic polyols and epichlorohydrin. Also suitable as polyols are polymers and copolymers that contain hydroxyl groups in the polymer chain or in side groups, e.g. polyvinyl alcohol and copolymers thereof or polymethacrylic acid hydroxyalkyl esters or copolymers thereof. Further suitable polyols are oligoesters having hydroxyl terminal groups.

Examples of aliphatic and cycloaliphatic polyols include alkylenediols having preferably from 2 to 12 carbon atoms, such as ethylene glycol, 1,2- or 1,3-propanediol, 1,2-, 1,3- or 1,4-butanediol, pentanediol, hexanediol, octanediol, dodecanediol, diethylene glycol, triethylene glycol, polyethylene glycols having molecular weights of preferably from 200 to 1500, 1,3-cyclopentanediol, 1,2-, 1,3- or 1,4-cyclohexanediol, 1,4-dihydroxymethylcyclohexane, glycerol, tris(β-hydroxyethyl)amine, trimethylolethane, trimethylolpropane, pentaerythritol, dipentaerythritol and sorbitol.

The polyols may be partially or fully esterified by one or by different unsaturated carboxylic acid(s), it being possible for the free hydroxyl groups in partial esters to be modified, for example etherified, or esterified by other carboxylic acids.

Examples of Esters are:
trimethylolpropane triacrylate, trimethylolethane triacrylate, trimethylolpropane trimethacrylate, trimethylolethane trimethacrylate, tetramethylene glycol dimethacrylate, triethylene glycol dimethacrylate, tetraethylene glycol diacrylate, pentaerythritol diacrylate, pentaerythritol triacrylate, pentaerythritol tetraacrylate, dipentaerythritol diacrylate, dipentaerythritol triacrylate, dipentaerythritol tetraacrylate, dipentaerythritol pentaacrylate, dipentaerythritol hexaacrylate, tripentaerythritol octaacrylate, pentaerythritol dimethacrylate, pentaerythritol trimethacrylate, dipentaerythritol dimethacrylate, dipentaerythritol tetramethacrylate, tripentaerythritol octamethacrylate, pentaerythritol diitaconate, dipentaerythritol trisitaconate, dipentaerythritol pentaitaconate, dipentaerythritol hexaitaconate, ethylene glycol diacrylate, 1,3-butanediol diacrylate, 1,3-butanediol dimethacrylate, 1,4-butanediol diitaconate, sorbitol triacrylate, sorbitol tetraacrylate, pentaerythritol-modified triacrylate, sorbitol tetramethacrylate, sorbitol pentaacrylate, sorbitol hexaacrylate, oligoester acrylates and methacrylates, glycerol di- and tri-acrylate, 1,4-cyclohexane diacrylate, bisacrylates and bismethacrylates of polyethylene glycol having a molecular weight of from 200 to 1500, and mixtures thereof.

Also suitable as component (A) are the amides of identical or different unsaturated carboxylic acids and aromatic, cycloaliphatic and aliphatic polyamines having preferably from 2 to 6, especially from 2 to 4, amino groups. Examples of such polyamines are ethylenediamine, 1,2- or 1,3-propylenediamine, 1,2-, 1,3- or 1,4-butylenediamine, 1,5-pentylenediamine, 1,6-hexylenediamine, octylenediamine, dodecylenediamine, 1,4-diaminocyclohexane, isophoronediamine, phenylenediamine, bisphenylenediamine, di-β-aminoethyl ether, diethylenetriamine, triethylenetetramine and di(β-aminoethoxy)- and di(β-aminopropoxy)-ethane. Further suitable polyamines are polymers and copolymers which may have additional amino groups in the side chain and oligoamides having amino terminal groups. Examples of such unsaturated amides are: methylene bisacrylamide, 1,6-hexamethylene bisacrylamide, diethylenetriamine trismethacrylamide, bis(methacrylamidopropoxy)ethane, β-methacrylamidoethyl methacrylate and N-[(β-hydroxyethoxy)ethyl]-acrylamide.

Suitable unsaturated polyesters and polyamides are derived, for example, from maleic acid and diols or diamines. The maleic acid may have been partially replaced by other dicarboxylic acids. They may be used together with ethylenically unsaturated comonomers, e.g. styrene. The polyesters and polyamides may also be derived from dicarboxylic acids and ethylenically unsaturated diols or diamines, especially from those having longer chains of e.g. from 6 to 20 carbon atoms. Examples of polyurethanes are those composed of saturated diisocyanates and unsaturated diols or unsaturated diisocyanates and saturated diols.

Polybutadiene and polyisoprene and copolymers thereof are known. Suitable comonomers include, for example, olefins, such as ethylene, propene, butene and hexene, (meth)acrylates, acrylonitrile, styrene and vinyl chloride. Polymers having (meth)acrylate groups in the side chain are likewise known. Examples are reaction products of novolak-based epoxy resins with (meth)acrylic acid; homo- or co-polymers of vinyl alcohol or hydroxyalkyl derivatives thereof that have been esterified with (meth)acrylic acid; and homo- and co-polymers of (meth)acrylates that have been esterified with hydroxyalkyl(meth)acrylates. (The term "(meth)acrylate" in the context of this Application denotes both "acrylate" and "methacrylate".)

Suitable components (A) are also acrylates that have been modified by reaction with primary or secondary amines, as described e.g. by Gaske in U.S. Pat. No. 3,844,916, by Weiss et al. in EP 280 222, by Meixner et al. in U.S. Pat. No. 5,482,649 or by Reich et al. in U.S. Pat. No. 5,734,002. Such amine-modified acrylates are also known as aminoacrylates. Aminoacrylates are obtainable e.g. from UCB Chemicals under the name EBECRYL 80, EBECRYL 81, EBECRYL 83, EBECRYL 7100, from BASF under the name Laromer PO 83F, Laromer PO 84F, Laromer PO 94F, from Cognis under the name PHOTOMER 4775 F, PHOTOMER 4967 F or from Cray Valley under the name CN501, CN503, CN550.

The photopolymerisable compounds can be used on their own or in any desired mixtures. Preferably mixtures of polyol(meth)acrylates are used.

Binders may also be added to the compositions according to the invention, this being particularly advantageous when the photopolymerisable compounds are liquid or viscous substances. The amount of binder may be, for example, from 5 to 95% by weight, preferably from 10 to 90% by weight and especially from 40 to 90% by weight, based on total solids. The choice of binder is made in accordance with the field of use and the properties required therefor, such as developability in aqueous and organic solvent systems, adhesion to substrates and sensitivity to oxygen.

Suitable binders are, for example, polymers having a molecular weight of approximately from 5000 to 2 000 000, preferably from 10 000 to 1 000 000. Examples are: homo- and copolymers of acrylates and methacrylates, e.g. copolymers of methyl methacrylate/ethyl acrylate/methacrylic acid, poly(methacrylic acid alkyl esters), poly(acrylic acid alkyl esters); cellulose esters and ethers, such as cellulose acetate, cellulose acetate butyrate, methylcellulose, ethylcellulose; polyvinylbutyral, polyvinylformal, cyclised rubber, polyethers such as polyethylene oxide, polypropylene oxide, polytetrahydrofuran; polystyrene, polycarbonate, polyurethane, chlorinated polyolefins, polyvinyl chloride, copolymers of vinyl chloride/vinylidene chloride, copolymers of vinylidene chloride with acrylonitrile, methyl methacrylate and vinyl acetate, polyvinyl acetate, copoly(ethylene/vinyl acetate), polymers such as polycaprolactam and poly(hexamethylene adipamide), polyesters such as poly(ethylene glycol terephthalate) and poly(hexamethylene glycol succinate).

The unsaturated compounds can also be used in admixture with non-photopolymerisable film-forming components. These may be, for example, physically drying polymers or solutions thereof in organic solvents, for example nitrocellulose or cellulose acetobutyrate, but they may also be chemically or thermally curable resins, for example polyisocyanates, polyepoxides or melamine resins. The concomitant use of thermally curable resins is important for use in so-called hybrid systems, which are photopolymerised in a first step and crosslinked by thermal after-treatment in a second step.

The mixtures according to the invention of compounds of formula (I) with photoinitiators are also suitable for the curing of oxidatively drying systems, as described e.g. in "Lehrbuch der Lacke und Beschichtungen" Vol. III, 296-328, Verlag W. A. Colomb in der Heenemann GmbH, Berlin-Oberschwandorf (1976).

The photopolymerisable mixtures may also comprise various additives (D) in addition to the photoinitiator. Examples thereof are thermal inhibitors, which are intended to prevent premature polymerisation, e.g. hydroquinone, hydroquinone derivatives, p-methoxyphenol, βnaphthol or sterically hindered phenols, e.g. 2,6-di(tert-butyl)-p-cresol. In order to increase dark-storage stability it is possible to use, for example, copper compounds, such as copper naphthenate, stearate or octoate, phosphorus compounds, for example triphenylphosphine, tributylphosphine, triethyl phosphite, triphenyl phosphite or tribenzyl phosphite, quaternary ammonium compounds, e.g. tetramethylammonium chloride or trimethylbenzylammonium chloride, or hydroxylamine derivatives, e.g. N-diethylhydroxylamine. For the purpose of excluding atmospheric oxygen during polymerisation it is possible to add paraffin or similar wax-like substances which, being insoluble in the polymer, migrate to the surface at the beginning of the polymerisation and form a transparent surface layer which prevents air from entering. Equally possible is the application of a layer that is impermeable to oxygen. As light stabilisers it is possible to add UV absorbers, e.g. those of the hydroxyphenylbenzotriazole, hydroxyphenylbenzophenone, oxalic acid amide or hydroxyphenyl-s-triazine type. Such compounds can be used on their own or in the form of mixtures, with or without the use of sterically hindered amines (HALS).

Suitable hydroxyphenyl-s-triazine compounds and sterically hindered amines (HALS) are known to the person skilled in the art and are widely described. Examples of the use of light stabilisers and UV absorbers in photocurable formulations are described, for example, by A. Valet in Farbe Lack 1990,96, 189.

It is also possible for additives customary in the art, for example antistatics, flow improvers and adhesion promoters, to be used.

In order to accelerate the photopolymerisation, as further additives (D) it is possible to add amines, e.g. triethanolamine, N-methyl-diethanolamine, p-dimethylaminobenzoic acid ethyl ester or Michler's ketone. The action of the amines can be enhanced by the addition of aromatic ketones of the benzophenone type. Amines suitable for use as oxygen capture agents are, for example, substituted N,N-dialkylanilines, as described in EP 339 841. Further accelerators, co-initiators and auto-oxidisers are thiols, thio ethers, disulfides and phosphines, as described e.g. in EP 438 123 and GB 2 180 358.

It is also possible for chain-transfer reagents customary in the art to be added to the compositions according to the invention. Examples are mercaptans, amines and benzothiazole.

Photopolymerisation can also be accelerated by the addition, as further additives (D), of photosensitisers (D1) that shift or broaden the spectral sensitivity. These include especially aromatic carbonyl compounds, e.g. benzophenone, thioxanthone, including especially isopropylthioxanthone, anthraquinone and 3-acylcoumarin derivatives, terphenyls, styryl ketones, and 3-(aroylmethylene)-thiazolines, camphorquinone and also eosin, rhodamine and erythrosine dyes.

Further examples of such photosensitisers (D1) are

1. Thioxanthones

Thioxanthone, 2-isopropylthioxanthone, 2-chlorothioxanthone, 1-chloro-4-propoxythioxanthone, 2-dodecylthioxanthone, 2,4-diethylthioxanthone, 2,4-dimethylthioxanthone, 1-methoxycarbonylthioxanthone, 2-ethoxycarbonylthioxanthone, 3-(2-methoxyethoxycarbonyl)-thioxanthone, 4-butoxycarbonylthioxanthone, 3-butoxycarbonyl-7-methylthioxanthone, 1-cyano-3-chlorothioxanthone, 1-ethoxycarbonyl-3-chlorothioxanthone, 1-ethoxycarbonyl-3-ethoxythioxanthone, 1-ethoxycarbonyl-3-aminothioxanthone, 1-ethoxycarbonyl-3-phenylsulfurylthioxanthone, 3,4-di[2-(2-methoxyethoxy)ethoxycarbonyl]thioxanthone, 1-ethoxycarbonyl-3-(1-methyl-1-morpholinoethyl)-thioxanthone, 2-methyl-6-dimethoxymethyl-thioxanthone, 2-methyl-6-(1,1-dimethoxybenzyl)-thioxanthone, 2-morpholinomethylthioxanthone, 2-methyl-6-morpholinomethylthioxanthone, N-allylthioxanthone-3,4-dicarboximide, N-octylthioxanthone-3,4-dicarboximide, N-(1,1,3,3-tetramethylbutyl)-thioxanthone-3,4-dicarboximide, 1-phenoxythioxanthone, 6-ethoxycarbonyl-2-methoxythioxanthone, 6-ethoxycarbonyl-2-methylthioxanthone, thioxanthone-2-polyethylene glycol ester, 2-hydroxy-3-(3,4-dimethyl-9-oxo-9H-thioxanthon-2-yloxy)-N,N,N-trimethyl-1-propanaminium chloride.

2. Benzophenones

Benzophenone, 4-phenylbenzophenone, 4-methoxybenzophenone, 4,4'-dimethoxybenzophenone, 4,4'-dimethylbenzophenone, 4,4'-dichlorobenzophenone, 4,4'-dimethylaminobenzophenone, 4,4'-diethylaminobenzophenone, 4-methylbenzophenone, 2,4,6-trimethylbenzophenone, 4-(4-methylthiophenyl)-benzophenone, 3,3'-dimethyl-4-methoxybenzophenone, methyl 2-benzoylbenzoate, 4-(2-hydroxyethylthio)-benzophenone, 4-(4-tolylthio)-benzophenone, 4-benzoyl-N,N,N-trimethylbenzenemethanaminium chloride, 2-hydroxy-3-(4-benzoylphenoxy)-N,N,N-trimethyl-1-propanaminium chloride monohydrate, 4-(13-acryloyl-1,4,7,10,13-pentaoxatridecyl)-benzophenone, 4-benzoyl-N,N-dimethyl-N-[2-(1-oxo-2-propenyl)oxy]ethyl-benzenemethanaminium chloride.

3. 3-Acylcoumarins

3-Benzoylcoumarin, 3-benzoyl-7-methoxycoumarin, 3-benzoyl-5,7-di(propoxy)coumarin, 3-benzoyl-6,8-dichlorocoumarin, 3-benzoyl-6-chlorocoumarin, 3,3'-carbonyl-bis [5,7-di(propoxy)coumarin], 3,3'-carbonyl-bis(7-methoxy-coumarin), 3,3'-carbonyl-bis(7-diethylaminocoumarin), 3-isobutyroylcoumarin, 3-benzoyl-5,7-dimethoxycoumarin, 3-benzoyl-5,7-diethoxycoumarin, 3-benzoyl-5,7-dibutoxy-coumarin, 3-benzoyl-5,7-di(methoxyethoxy)-coumarin, 3-benzoyl-5,7-di(allyloxy)coumarin, 3-benzoyl-7-dimethylaminocoumarin, 3-benzoyl-7-diethylaminocoumarin, 3-isobutyroyl-7-dimethylaminocoumarin, 5,7-dimethoxy-3-(1naphthoyl)-coumarin, 5,7-dimethoxy-3-(1-naphthoyl) coumarin, 3-benzoylbenzo[f]coumarin, 7-diethylamino-3-thienoylcoumarin, 3-(4-cyanobenzoyl)-5,7-dimethoxycoumarin.

4. 3-(Aroylmethylene)-thiazolines

3-Methyl-2-benzoylmethylene-β-naphthothiazoline, 3-methyl-2-benzoylmethylene-benzothiazoline, 3-ethyl-2-propionylmethylene-β-naphthothiazoline.

5. Other Carbonyl Compounds

Acetophenone, 3-methoxyacetophenone, 4-phenylacetophenone, benzil, 2-acetylnaphthalene, 2-naphthaldehyde, 9,10-anthraquinone, 9-fluorenone, dibenzosuberone, xanthone, 2,5-bis(4-diethylaminobenzylidene)cyclopentanone, α-(paradimethylaminobenzylidene)ketones, such as 2-(4-dimethylamino-benzylidene)-indan-1-one or 3-(4-dimethylamino-phenyl)-1-indan-5-yl-propenone, 3-phenylthiophthalimide, N-methyl-3,5-di(ethylthio)phthalimide, N-methyl-3,5-di(ethylthio)phthalimide, poly(propylene glycol)-4-(dimethylamino)benzoate.

6. Anthracenes

Anthracene, 9-phenylanthracene, 9,10-dimethoxyanthracene, 9,10-dimethoxy-2-ethylanthracene, 9,10-diethoxyanthracene, 9-methoxyanthracene, 9-methylanthracene, 9,10-dimethylanthracene, 9-vinylanthracene, 9,10-anthracene dicarbonitrile, 9,10-diphenylanthracene, (9-anthryl)methacrylate, 9-acetylanthracene, 9-anthracenemethanol, 7,12-dimethylbenz[a]anthracene, 9,10-bis(phenylethynyl)anthracene.

The curing process, especially in the case of pigmented compositions (e.g. compositions pigmented with titanium dioxide), may also be assisted by the addition, as additional additive (D), of a component that forms free radicals under thermal conditions, e.g. an azo compound, such as 2,2'-azobis(4-methoxy-2,4-dimethylvaleronitrile), a triazene, diazosulfide, pentazadiene or a peroxy compound, for example a hydroperoxide or peroxycarbonate, e.g. tert-butyl hydroperoxide, as described e.g. in EP 245 639.

The compositions according to the invention may also comprise as further additives (D) a photoreducible dye, e.g. a xanthene, benzoxanthene, benzothioxanthene, thiazine, pyronin, porphyrin or acridine dye, and/or a radiation-cleavable trihalomethyl compound. Similar compositions are described, for example, in EP 445 624.

Further customary additives (D) are—depending upon the intended use—optical brighteners, fillers, pigments, both white and colored pigments, colorants, antistatics, wetting agents or flow improvers.

For curing thick and pigmented coatings it is suitable to add glass microbeads or pulverised glass fibers, as described e.g. in U.S. Pat. No. 5,013,768.

The formulations may also comprise colorants and/or white or colored pigments. Depending upon the intended use, both inorganic and organic pigments may be used. Such additives will be known to the person skilled in the art; some examples are titanium dioxide pigments, e.g. of the rutile or anatase type, carbon black, zinc oxide, such as zinc white, iron oxides, such as iron oxide yellow, iron oxide red, chromium yellow, chromium green, nickel titanium yellow, ultramarine blue, cobalt blue, bismuth vanadate, cadmium yellow and cadmium red. Examples of organic pigments are mono- or bis-azo pigments, and also metal complexes thereof, phthalocyanine pigments, polycyclic pigments, e.g. perylene, anthraquinone, thioindigo, quinacridone or triphenylmethane pigments, and also diketo-pyrrolo-pyrrole, isoindolinone, e.g. tetrachloroisoindolinone, isoindoline, dioxazine, benzimidazolone and quinophthalone pigments. The pigments may be used in the formulations on their own or in admixture.

Depending upon the intended use, the pigments are added to the formulations in amounts customary in the art, for example in an amount of from 0.1 to 60% by weight, or from 10 to 30% by weight, based on the total mass.

The formulations may also comprise, for example, organic colorants of an extremely wide variety of classes. Examples are azo dyes, methine dyes, anthraquinone dyes and metal complex dyes. Customary concentrations are, for example, from 0.1 to 20%, especially from 1 to 5%, based on the total mass.

The choice of additives is governed by the field of use in question and the properties desired for that field. The additives (D) described above are customary in the art and are accordingly used in the amounts customary in the art.

The invention relates also to compositions comprising as component (A) at least one ethylenically unsaturated photopolymerisable compound dissolved or emulsified or dispersed in water.

Radiation-curable aqueous prepolymer dispersions are commercially available in many variations and are to be understood as being dispersions containing water as continuous phase and at least one prepolymer dispersed therein. The radiation-curable prepolymer or prepolymer mixture is present dispersed in water in concentrations of from 20 to 95% by weight, especially from 30 to 70% by weight. In such compositions the sum of the percentages of water and prepolymer or prepolymer mixture is 100 in each case, auxiliaries and additives (e.g. emulsifiers), which are present in varying amounts in accordance with the intended use, being in addition thereto.

The radiation-curable aqueous prepolymer dispersions are known polymer systems that comprise mono- or polyfunctional ethylenically unsaturated prepolymers having an average molecular weight $M_n$ (in g/mol) of at least 400, especially from 500 to 100 000. Prepolymers having higher molecular weights may also be suitable, however, depending upon the intended use.

There are used, for example, polymerisable C—C double-bond-containing polyesters having an acid number of a maximum of 10, polymerisable C—C double-bond-containing polyethers, hydroxyl-group-containing reaction products of a polyepoxide containing at least two epoxy groups per molecule with at least one α,β-ethylenically unsaturated carboxylic acid, polyurethane(meth)acrylates and acrylic copolymers containing α,β-ethylenically-unsaturated acrylic radicals, as described in EP 12 339. Mixtures of those prepolymers may also be used.

Also suitable are the polymerisable prepolymers described in EP 33 896, which are thio ether adducts having an average molecular weight $M_n$ (in g/mol) of at least 600, which likewise contain polymerisable C—C double bonds. Other suitable aqueous polymer dispersions based on specific (meth)acrylic acid alkyl ester polymerisation products are described in EP 41 125.

As further additives, such radiation-curable aqueous prepolymer dispersions may comprise dispersing agents, emulsifiers, anti-oxidants, light stabilisers, colorants, pigments, fillers, e.g. talcum, gypsum, silicic acid, rutile, carbon black, zinc oxide, iron oxides, reaction accelerators, flow agents, lubricants, wetting agents, thickeners, dulling agents, antifoams and other adjuvants customary in surface-coating technology. Suitable dispersing agents include water-soluble high molecular weight organic compounds having polar groups, e.g. polyvinyl alcohols, polyvinylpyrrolidone and cellulose ethers. As emulsifiers it is possible to use non-ionic and, where appropriate, also ionic emulsifiers.

In certain cases it may be advantageous to use mixtures of two or more photoinitiators, e.g. mixtures with camphor quinone, benzophenone, benzophenone derivatives, 2,4,6-trimethylbenzophenone, 2-methylbenzophenone, 3-methylbenzophenone, 4-methylbenzophenone, 4,4'-bis(chloromethyl)benzophenone, 4-chlorobenzophenone, 4-phenylbenzophenone, 3,3'-dimethyl-4-methoxy-benzophenone, [4-(4-methylphenylthio)phenyl]-phenylmethanone, methyl-2-benzoyl benzoate, acetophenone, acetophenone derivatives, for example α-hydroxycycloalkylphenyl ketones or 2-hydroxy-2-methyl-1-phenyl-propanone, dialkoxyacetophenones, α-hydroxy- or α-amino-acetophenones, e.g. (4-methylthiobenzoyl)-1-methyl-1-morpholino-ethane, 4-aroyl-1,3-dioxolanes, benzoin alkyl ethers and benzil ketals, e.g. benzil dimethyl ketal phenyl glyoxalates and derivatives thereof, dimeric phenyl glyoxylates, peresters, e.g. benzophenonetetracarboxylic acid peresters, such as described, for example, in EP 126 541, monoacylphosphine oxides, e.g. (2,4,6-trimethylbenzoyl)-phenylphosphine oxide, bisacylphosphine oxides, e.g. bis(2,6-dimethoxybenzoyl)-(2,4,4-trimethylpent-1-yl)phosphine oxide, bis(2,4,6-trimethylbenzoyl)-phenyl-phosphine oxide or bis(2,4,6-trimethylbenzoyl)-(2,4-dipentyloxyphenyl)phosphine oxide, trisacylphosphine oxides, halomethyltriazines, e.g. 2-[2-(4-methoxy-phenyl)-vinyl]-4,6-bis-trichloromethyl[1,3,5]triazine, 2-(4-methoxy-phenyl)-4,6-bis-trichloromethyl[1,3,5]triazine, 2-(3,4-dimethoxy-phenyl)-4,6-bis-trichloromethyl[1,3,5]triazine, 2-methyl-4,6-bis-trichloromethyl-[1,3,5]triazine, hexaarylbisimidazole/coinitiator systems, e.g. ortho-chlorohexaphenyl-bisimidazole in combination with 2-mercaptobenzothiazole; ferrocenium compounds or titanocenes, for example dicyclopentadienyl-bis(2,6-difluoro-3-pyrrolo-phenyl)-titanium. It is also possible to use borate compounds as coinitiators.

When hybrid systems are used, in addition to the free-radical hardeners there are also used cationic photoinitiators, e.g. benzoyl peroxide (other suitable peroxides are described in U.S. Pat. No. 4,950,581, column 19, lines 17-25), aromatic sulfonium, phosphonium or iodonium salts, as described e.g. in U.S. Pat. No. 4,950,581, column 18, line 60 to column 19, line 10, or cyclopentadienylarene-iron(II) complex salts, e.g. ($\eta^6$-isopropylbenzene)($\eta^5$-cyclopentadienyl)iron(II) hexafluorophosphate.

The photopolymerisable compositions comprise the photoinitiator advantageously in an amount of from 0.05 to 20% by weight, preferably from 0.1 to 5% by weight, based on the composition. The amount of photoinitiator indicated relates to the sum of all added photoinitiators when mixtures thereof are used, that is to say both to the photoinitiator (B) and to the photoinitiators (B)+(C).

The photopolymerisable compositions may be used for a variety of purposes, for example as printing inks, such as screen printing inks, flexographic printing inks and offset printing inks, as clearcoats, as colored coats, as whitecoats, for example for wood or metal, as powder coatings, as coating materials inter alia for paper, wood, metal or plastics, as daylight-curable paints for marking structures and roads, for photographic reproduction processes, for holographic recording materials, for image-recording processes or in the production of printing plates that can be developed using organic solvents or using aqueous-alkaline media, in the production of masks for screen printing, as dental filling compounds, as adhesives, as pressure-sensitive adhesives, as laminating resins, as photoresists, e.g. galvanoresists, etch resists or permanent resists, both liquid and dry films, as photostructurable dielectrics, and as solder masks for electronic circuits, as resists in the production of color filters for any type of display screen or in the creation of structures during the production of plasma displays and electroluminescent displays, in the production of optical switches, optical gratings (interference gratings), in the production of three-dimensional articles by bulk curing (UV curing in transparent moulds) or according to the stereolithography process, as described, for example, in U.S. Pat. No. 4,575,330, in the production of composite materials (e.g. styrene polyesters which may include glass fibers and/or other fibers and other adjuvants) and other thick-layered compositions, in the coating or sealing of electronic components or as coatings for optical fibers. The compositions are also suitable for the production of optical lenses, e.g. contact lenses or Fresnel lenses, and also for the production of medical apparatus, aids or implants.

The compositions are also suitable for the preparation of gels having thermotropic properties. Such gels are described e.g. in DE 197 00 064 and EP 678 534.

The compositions can also be used in dry film paints, as described e.g. in Paint & Coatings Industry, April 1997, 72 or Plastics World, Vol. 54, No. 7, page 48(5).

The photoinitiators in admixture with compounds of formula (I) can also be used as initiators for emulsion, bead or suspension polymerisation or as initiators of a polymerisation step for fixing orientation states of liquid-crystalline monomers and oligomers or as initiators for fixing dyes on organic materials.

In surface coatings, use is frequently made of mixtures of a prepolymer with polyunsaturated monomers that also comprise a mono unsaturated monomer, the prepolymer in particular determining the properties of the surface-coating film, so that a person skilled in the art will be able to influence the properties of the cured film by varying the prepolymer. The polyunsaturated monomer functions as a crosslinking agent, which renders the surface-coating film insoluble. The monounsaturated monomer functions as a reactive diluent, by means of which the viscosity is reduced without the need to use a solvent.

Unsaturated polyester resins are generally used in two-component systems together with a monounsaturated monomer, preferably styrene. For photoresists, specific one-component systems are often used, e.g. polymaleinimides, polychalcones or polyimides, as described in DE 2 308 830.

The photoinitiators in admixture with compounds of formula (I) can also be used as free-radical photoinitiators or photoinitiating systems for radiation-curable powder coatings. The powder coatings can be based on solid resins and monomers containing reactive double bonds, for example maleates, vinyl ethers, acrylates, acrylamides and mixtures thereof. A free-radically UV-curable powder coating can be formulated by mixing unsaturated polyester resins with solid acrylamides (e.g. methylacrylamidoglycolate methyl ester) and a photoinitiator in admixture with compounds of formula (I), as described, for example, in the presentation "Radiation Curing of Powder Coating", Conference Proceedings, Radtech Europe 1993 by M. Wittig and T h. Gohmann. Similarly, free-radically UV-curable powder coatings can be formulated by mixing unsaturated polyester resins with solid acrylates, methacrylates or vinyl ethers and a photoinitiator in admixture with compounds of formula (I). The powder coatings may also comprise binders, as described, for example, in DE 4 228 514 and EP 636 669. The UV-curable powder coatings may also comprise white or colored pigments. For example, especially rutile/titanium dioxide may be used in concentrations of up to 50% by weight in order to obtain a cured powder coating having good hiding power. The process normally comprises spraying the powder electrostatically or tribostatically onto the substrate, for example metal or wood, melting the powder by heating and, after a smooth film has formed, radiation-curing the coating with ultraviolet and/or visible light, for example using medium-pressure mercury lamps, metal halide lamps or xenon lamps. A particular advantage of radiation-curable powder coatings over corresponding thermally curable coatings is that the flow time after the powder particles have been melted can be prolonged as desired in order to ensure the formation of a smooth high-gloss coating. Unlike thermally curable systems, radiation-curable powder coatings can be so formulated that they melt at relatively low temperatures without the undesired effect of their useful life being shortened. For that reason they are also suitable as coatings for heat-sensitive substrates, such as wood or plastics.

In addition to the photoinitiators and compounds of formula (I) according to the invention the powder coating formulations may also comprise UV absorbers. Appropriate examples are listed hereinabove.

The photocurable compositions according to the invention are suitable, for example, as coating materials for all kinds of substrate, for example wood, textiles, paper, ceramics, glass, plastics, such as polyesters, polyethylene terephthalate, polyolefins and cellulose acetate, especially in the form of films, and also metals, such as Al, Cu, Ni, Fe, Zn, Mg or Co and GaAs, Si or $SiO_2$, to which a protective layer is to be applied or an image is to be applied e.g. by imagewise exposure.

The substrates can be coated by applying a liquid composition, a solution or a suspension to the substrate. The choice of solvent and its concentration are governed chiefly by the nature of the composition and the coating method. The solvent should be inert, that is to say it should not enter into any chemical reaction with the components, and it should be capable of being removed again on drying after the coating operation. Suitable solvents include, for example, ketones, ethers and esters, such as methyl ethyl ketone, isobutyl methyl ketone, cyclopentanone, cyclohexanone, N-methylpyrrolidone, dioxane, tetrahydrofuran, 2-methoxyethanol, 2-ethoxyethanol, 1-methoxy-2-propanol, 1,2-dimethoxyethane, ethyl acetate, n-butyl acetate and ethyl 3-ethoxypropionate.

The formulation is applied uniformly to a substrate by means of known coating methods, for example by spin-coating, immersion, knife coating, curtain pouring, brush application or spraying, especially by electrostatic spraying and reverse-roll coating, and also by electrophoretic deposition. It is also possible to apply the photosensitive layer to a temporary flexible support and then coat the final substrate, e.g. a copper-clad circuit board, by transferring the layer via lamination.

The amount applied (layer thickness) and the nature of the substrate (layer support) are dependent upon the desired field of application. The range of layer thicknesses generally includes values from about 0.1 µm to more than 100 µm, for example 20 µm or from 0.02 to 10 mm, e.g. from 1 to 10 µm. The radiation-sensitive compositions according to the invention are used, for example, as negative resists that have a very high degree of photosensitivity and can be developed in an aqueous-alkaline medium without swelling. They are suitable as photoresists for electronics, such as galvanoresists, etch resists, in both liquid and dry films, as solder resists, as resists in the production of color filters for any type of display screen, or in the formation of structures during the production of plasma displays and electroluminescent displays, in the production of printing plates, such as offset printing plates, in the production of printing blocks for letterpress printing, planographic printing, intaglio printing, flexographic printing or screen printing blocks, the production of relief copies, e.g. for the production of texts in braille, in the production of dies, for use in the etching of mouldings or for use as microresists in the production of integrated circuits. The compositions can also be used as photostructurable dielectrics, for the encapsulation of materials or as insulator coating in the production of computer chips, printed circuits and other electrical or electronic components. The layer supports that are possible and the conditions for processing the coated substrates are correspondingly various.

Conjugated polymers, e.g. polyanilines, can be converted from a semi-conductive state to a conductive state by doping with protons. The photoinitiators according to the invention can also be used for the imagewise exposure of polymerisable compositions comprising such polymers in order to form conductive structures (in the irradiated zones) which are embedded in insulating material (non-exposed zones). Such materials can be used, for example, as wiring components or connecting components in the production of electrical or electronic components.

The compounds according to the invention are also used in the production of single- or multi-layer materials for image recording or image duplication (copying, reprographics), which may be monochrome or polychrome. Those materials can also be used in color-testing systems. In that technology it is also possible to use formulations containing microcapsules, and for creating the image the exposure step can be followed by a thermal step. Such systems and technologies and their use are described e.g. in U.S. Pat. No. 5,376,459.

For photographic information recordings there are used, for example, foils of polyester, cellulose acetate or plastics-coated papers; for offset printing blocks e.g. specially treated aluminium, in the production of printed circuits e.g. copper-clad laminates, and in the production of integrated circuits silicon wafers. The layer thicknesses for photographic materials and offset printing blocks are generally about from 0.5 µm to 10 µm, and for printed circuits from 1.0 µm to about 100 µm.

After the substrates have been coated, the solvent is generally removed by drying, resulting in a layer of photoresist on the support.

The term "imagewise" exposure includes both exposure through a photomask having a predetermined pattern, e.g. a transparency, exposure using a laser beam which is moved over the surface of the coated substrate, for example under computer control, and in that way produces an image, and irradiation with computer-controlled electron beams. It is also possible to use masks of liquid crystals which can be actuated pixel by pixel in order to create digital images, as described e.g. by A. Bertsch, J. Y. Jezequel, J. C. Andre in Journal of Photochemistry and Photobiology A: Chemistry 1997, 107, pp. 275-281 and by K.-P. Nicolay in Offset Printing 1997, 6, pp. 34-37.

After the imagewise exposure of the material and prior to development it may be advantageous to carry out a thermal treatment for a relatively short time. During the thermal treatment only the exposed areas are thermally cured. The temperatures used are generally from 50 to 150° C., preferably from 80 to 130° C.; the duration of the thermal treatment is generally from 0.25 to 10 minutes.

After the exposure and optional thermal treatment, the unexposed areas of the photosensitive coating are removed using a developer in a manner known per se.

As already mentioned, the compositions according to the invention can be developed in an aqueous-alkaline medium. Suitable aqueous-alkaline developer solutions are especially aqueous solutions of tetraalkylammonium hydroxides or of alkali metal silicates, phosphates, hydroxides and carbonates. If desired, relatively small amounts of wetting agents and/or organic solvents may be added to those solutions. Typical organic solvents that may be added in small amounts to the developer fluids are, for example, cyclohexanone, 2-ethoxyethanol, toluene, acetone and mixtures of such solvents.

Photocuring is of great importance for printing inks, since the drying time of the binder is a determining factor in the rate of production of graphic products and should be of the order of fractions of a second. UV-curable inks are important especially for screen printing.

As already mentioned above, the mixtures according to the invention are also very suitable for the production of printing plates. For that application there are used, for example, mixtures of soluble linear polyamides or styrene/butadiene or styrene/isoprene rubber, polyacrylates or polymethyl methacrylates having carboxyl groups, polyvinyl alcohols or urethane acrylates with photopolymerisable monomers, for example acrylic or methacrylic amides or acrylic or methacrylic esters, and a photoinitiator. Films and plates made from those systems (wet or dry) are exposed through the negative (or positive) of the original and the uncured portions are then eluted with a suitable solvent.

Another field of use for photocuring is metal coating, for example in the application of a finish to sheets and tubes, cans or bottle closures, as well as photocuring on plastics coatings, for example of PVC-based floor or wall coverings.

Examples of the photocuring of paper coatings include the application of a colorless finish to labels, packaging materials or book covers.

Also of possible interest is the use of photoinitiators in admixture with compounds of formula (I) according to the invention in the curing of mouldings made of composite materials.

The photoinitiators in combination with compounds of formula (I) are also suitable for use in compositions for the coating of glass fibers (optical fibers). Such fibers are usually provided with protective coats immediately after their production. The glass fiber is drawn and then one or more coatings are applied to the glass filament. One, two or three layers are generally applied, the uppermost coating (top coating), for example, being colored ("ink layer" or "ink coating"). Furthermore, a plurality of fibers so coated are generally assembled into a bundle and coated, that is to say a glass fiber cable is formed. The compositions of the present Application are generally suitable for all of the above-described coatings of such cables; they need to have good properties in respect of pliability over a wide temperature range, tensile strength, loadability and toughness, and also rapid UV-curing characteristics.

Each of the coats—the inner, first coat, the "primary coating" (usually a pliable, soft coating), the outer first or second coat, the "secondary coating" (usually a firmer coating than the inner coat), the third or cable-forming coat (cabling coat)—may comprise at least one radiation-curable oligomer, at least one radiation-curable monomer, at least one photoinitiator in combination with compounds of formula (I), as well as additives.

In general any radiation-curable oligomers are suitable. Preference is given to oligomers having a molecular weight of at least 500, for example from 500 to 10 000, from 700 to 10 000, from 1000 to 8000 or from 1000 to 7000, especially urethane oligomers having at least one unsaturated group. Preferably the radiation-curable oligmer component has two terminal functional groups. The coat may contain a specific oligomer or a mixture of different oligomers. The preparation of suitable oligomers is known to the person skilled in the art and disclosed, for example, in U.S. Pat. No. 6,136,880. The oligomers are obtained, for example, by reaction of an oligomeric diol, preferably a diol having from 2 to 10 polyoxaalkylene groups, with a diisocyanate or a polyisocyanate and a hydroxy-functional ethylenically unsaturated monomer, for example hydroxyalkyl (meth)acrylate. Specific examples of each of those components, as well as suitable quantity ratios of the components, can be found in U.S. Pat. No. 6,136,880.

The addition of the radiation-curable monomer can be used, for example, to control the viscosity of the formulations. Accordingly, there is usually employed a low viscosity monomer having at least one functional group suitable for radiation-curable polymerisation. The amount is, for example, so chosen that a viscosity range of from 1000 to 10 000 mPas is achieved, that is to say usually from 10 to 90% by weight or from 10 to 80% by weight are used. The functional group of the monomer diluent is preferably of the same kind as that of the oligomer component, e.g. an acrylate or vinyl ether function and a higher alkyl or polyether moiety. Examples of monomer diluents suitable as constituents of compositions for coating optical fibers (glass fibers) are published, for example, in U.S. Pat. No. 6,136,880, column 12, line 11ff.

The first coat, the "primary coating", preferably comprises monomers having an acrylate or vinyl ether function and a polyether moiety having e.g. from 4 to 20 carbon atoms. Specific examples can be found in the US patent mentioned above.

The composition can also comprise, for example, a poly (siloxane), as described in U.S. Pat. No. 5,595,820, in order to improve the adhesive properties of the formulation to the glass fiber.

The coating compositions usually comprise further additives in order to prevent discoloration of the coating, especially during the production process, and to improve the stability of the cured coat. Examples are antioxidants, light stabilisers, UV absorbers, for example as described above, especially ®IRGANOX 1035, 1010, 1076, 1222, ®TINUVIN P, 234, 320, 326, 327, 328, 329, 213, 292, 144, 622LD (all Ciba Spezialitätenchemie), ®ANTIGENE P, 3C, FR, GA-80, ®SUMISORB TM-061 (Sumitomo Chemical Industries Co.), ®SEESORB 102, 103, 501, 202, 712, 704 (Sypro Chemical Co., Ltd.), ®SANOL LS770 (Sankyo Co. Ltd.). Particularly interesting are stabiliser combinations of sterically hindered piperidine derivatives (HALS) and sterically hindered phenol compounds, e.g. a combination of IRGANOX 1035 and TINUVIN 292, for example in a ratio of 1:1. Further additives are, for example, wetting agents or other additives having an effect on the rheological properties of the coating. Amines, e.g. diethylamine, can also be added.

Other examples of additives that can be used in compositions for the coating of optical fibers are silane crosslinking agents, e.g. γ-aminopropyltriethoxysilane, γ-mercaptopropyltrimethoxysilane, γ-methacryloxypropyl-trimethoxysilane, SH6062, SH6030 (Toray-Dow Corning Silicone Co., Ltd.), KBE 903, KBE 603, KBE 403 (Shin-Etsu Chemical Co., Ltd.).

In order to prevent discoloration of the coatings it is also possible for e.g. fluorescent additives or optical brighteners, e.g. ®UVITEX OB, from Ciba Spezialitätenchemie, to be added to the compositions.

For use in coatings for optical fibers, the photoinitiators in combination with compounds of formula (I) can of course also be used in admixture with one or more other photoinitiators, especially with mono- or bis-acylphosphine oxides, e.g. diphenyl-2,4,6-trimethylbenzoylphosphine oxide, bis(2, 4,6-trimethylbenzoyl)-phenylphosphine oxide (®IRGACURE 819), bis(2,6-dimethoxybenzoyl)-2,4,4-trimethylpentylphosphine oxide; α-hydroxyketones, e.g. 1-hydroxycyclohexylphenyl ketone (®IRGACURE 184), 2-hydroxy-2-methyl-1-phenyl-1-propanone (®DAROCUR 1173), 2-hydroxy-1-[4-(2-hydroxyethoxy)phenyl]-2-methyl-1-propanone (®IRGACURE 2959); α-aminoketones, e.g. 2-methyl-1-[4-(methylthio)phenyl]-2-(4-morpholinyl)-1-propanone (®IRGACURE 907); benzophenones, e.g. benzophenone, 2,4,6-trimethylbenzophenone, 4-methylbenzophenone, 2-methylbenzophenone, 2-methoxycarbonylbenzophenone, 4,4'-bis(chloromethyl)benzophenone, 4-chlorobenzophenone, 4-phenylbenzophenone, 4,4'-bis(dimethylamino)benzophenone, 4,4'-bis(diethylamino)benzophenone, methyl 2-benzoyl benzoate, 3,3'-dimethyl-4-methoxybenzophenone, 4-(4-methylphenylthio) benzophenone and also ketal compounds, e.g. 2,2-dimethoxy-1,2-diphenyl-ethanone (®IRGACURE 651); monomeric or dimeric phenylglyoxylic acid esters, e.g. methylphenylglyoxylic acid ester, 5,5'-oxo-di(ethyleneoxydicarbonylphenyl) or 1,2-(benzoylcarboxy)ethane. Especially suitable are mixtures with mono- or bis-acylphosphine oxides and/or α-hydroxyketones.

It will be evident that in order to enhance the properties of the photoinitiators the formulations may also comprise sensitiser compounds, e.g. amines.

The coatings are usually applied either "wet on dry" or "wet on wet". In the first case, after the application of the first coating (primary coat) a curing step by irradiation with UV light is carried out before the second layer is applied. In the second case, the two coatings are applied and cured together by means of irradiation with UV light.

For this application, the curing with UV light is usually carried out in a nitrogen atmosphere. In general all radiation sources customarily used in photocuring technology can also be used for curing the coatings of the optical fibers, that is to say, for example, radiation sources as described hereinbelow. Usually mercury medium pressure lamps or/and fusion D lamps are used. Flash lamps are also suitable. It will be clear that the emission spectrum of the lamps has to be matched to the absorption spectrum of the photoinitiator or photoinitiator mixture used. The compositions for coating optical fibers can likewise be cured by irradiation with electron beams, especially with low energy electron beams, for example as described in WO 98/41484.

In order to be able to differentiate different fibers in an arrangement of several fibers, the fibers can be provided, for example, with a third, colored coat ("ink coating"). The compositions used for such coatings comprise, in addition to the polymerisable components and the photoinitiator, a pigment or/and a dye. Examples of pigments suitable in such coatings are inorganic pigments, e.g. titanium dioxide, zinc oxide, zinc sulfide, barium sulfate, aluminium silicate, calcium silicate, carbon, black iron oxide, black copper chromite, iron oxides, green chromium oxides, iron blue, chromium green, violet (e.g. manganese violet, cobalt phosphate, $CoLiPO_4$), lead chromates, lead molybdates, cadmium titanates and pearlescent and metallic pigments, and also organic pigments, e.g. monoazo pigments, diazo pigments, diazo condensation pigments, quinacridone pigments, dioxazine violet, vat dyes, perylene pigments, thioindigo pigments, phthalocyanine pigments and tetrachloroisoindolinones. Examples of suitable pigments are carbon for black coatings, titanium dioxide for white coatings, diarylide yellow or pigments based on diazo compounds for yellow coatings, phthalocyanine blue and other phthalocyanines for blue coatings, anthraquinone red, naphthol red, pigments based on monoazo compounds, quinacridone pigments, anthraquinone and perylenes for red coatings, phthalocyanine green and pigments based on nitroso compounds for green coatings, pigments based on monoazo and diazo compounds, quinacridone pigments, anthraquinones and perylenes for orange coatings, and quinacridone violet, basic dye pigments and pigments based on carbazole dioxazine for violet coatings. The person skilled in the art will be familiar with the formulation and mixing of any further suitable pigments and dyes for the purpose of obtaining further colored coatings, for example light blue, brown, grey, pink etc.

The average particle size of the pigments is usually about 1 μm or less. If necessary, the size of commercially available pigments can be reduced, for example by milling. The pigments can be added to the formulations in the form of a dispersion, for example, in order to facilitate mixing with the other constituents of the formulation. The pigments are dissolved, for example, in a low viscosity liquid, e.g. a reactive diluent. It is usually preferred to use organic pigments. The proportion of pigments in a colored coating is, for example, from 1 to 20% by weight, from 1 to 15% by weight, preferably from 1 to 10% by weight. The colored coating generally also comprises a lubricant in order to improve the properties in respect of break-out of the individual coated fibers from the matrix. Examples of such lubricants are silicones, fluorohydrocarbon oils or resins etc.; especially silicone oils or functionalised silicone compounds, e.g. silicone diacrylate, are used.

The compositions of the present Application are also suitable as matrix material for an arrangement of coated optical fibers. That is to say, different fibers provided with a first, second (and in some cases a third, optionally colored) coat are brought together in a matrix. The coating for such an arrangement of different coated optical fibers (assembly) usually comprises, in addition to the additives already described above, a release agent in order to ensure access to the individual fibers, for example during installation of the cable. Examples of such release agents are Teflon, silicones, silicone acrylates, fluorohydrocarbon oils and resins etc. Such additives are usually used in amounts of from 0.5 to 20% by weight. Examples of colored coatings (ink coatings) and matrix materials for coated optical fibers can be found e.g. in U.S. Pat. Nos. 6,197,422 and 6,130,980 and in EP 614 099.

The compositions according to the invention can also be used in the production of light waveguides and optical switches, where the generation of a difference in refractive index between exposed and non-exposed regions is utilised.

Also important is the use of photocurable compositions for imaging processes and for the optical production of information carriers. For that application, as already described above, the layer (wet or dry) applied to the support is irradiated with UV or visible light through a photomask and the unexposed areas of the layer are removed by treatment with a solvent (=developer). The photocurable layer can also be applied to metal in an electrodeposition process. The exposed areas are crosslinked-polymeric and are therefore insoluble and remain on the support. When suitably colored, visible images are formed. When the support is a metallised layer, after exposure and development the metal can be etched away in the unexposed areas or strengthened by electroplating. In this way it is possible to produce printed electronic circuits and photoresists.

The photosensitivity of the compositions according to the invention usually extends from approximately 150 nm to approximately 600 nm (UV range). Suitable radiation is present, for example, in sunlight or light from artificial light sources. Accordingly a large number of the most varied kinds of light source may be used. Both point sources and planiform radiators (lamp arrays) are suitable. Examples are: carbon arc lamps, xenon arc lamps, medium pressure, super high pressure, high pressure and low pressure mercury radiators, doped, where appropriate, with metal halides (metal halide lamps), microwave-excited metal vapour lamps, excimer lamps, superactinic fluorescent tubes, fluorescent lamps, argon incandescent lamps, flash lamps, photographic floodlight lamps, light-emitting diodes (LED), electron beams and X-rays. The distance between the lamp and the substrate being exposed may vary according to the intended use and the type and strength of the lamp and may be, for example, from 2 cm to 150 cm. Especially suitable are laser light sources, for example excimer lasers, such as Krypton-F lasers, for exposure at 248 nm. Lasers in the visible range may also be used. According to this method it is possible to produce printed circuits in the electronics industry, lithographic offset printing plates or relief printing plates and also photographic image-recording materials.

The invention therefore relates also to a process for the photopolymerisation of non-volatile monomeric, oligomeric or polymeric compounds having at least one ethylenically unsaturated double bond, wherein a composition as described above is irradiated with light in a range of from 200 to 600 nm.

The invention relates also to the use of a composition as described above in the production of pigmented and non-pigmented surface coatings, printing inks, screen-printing inks, offset printing inks, flexographic printing inks, UV-curable ink-jet inks, powder coatings, printing plates, adhesives, dental compounds, light waveguides, optical switches, color-testing systems, composite materials, glass fiber cable coatings, screen-printing stencils, resist materials, color filters, gel coats (fine layers), for encapsulating electrical and electronic components, in the production of magnetic recording materials, in the production of three-dimensional articles by means of stereolithography, in the production of photographic reproductions, image-recording material, for holographic recordings, in the production of decolorising materials, in the production of decolorising materials for image-recording materials, in the production of image-recording materials using microcapsules, and to a process for the production of pigmented and non-pigmented surface coatings, printing inks, screen-printing inks, offset printing inks, flexographic printing inks, powder coatings, UV-curable ink-jet inks, printing plates, adhesives, dental compounds, light waveguides, optical switches, color-testing systems, composite materials, glass fiber cable coatings, screen-printing stencils, resist materials, color filters, gel coats (fine layers), for encapsulating electrical and electronic components, for the production of magnetic recording materials, for the production of three-dimensional articles by means of stereolithography, for the production of photographic reproductions, image-recording material, for holographic recordings, for the production of decolorising materials, for the production of decolorising materials for image-recording materials, for the production of image-recording materials using microcapsules.

The invention relates also to a coated substrate that has been coated on at least one surface with a free-radical-photopolymerisable or base-catalysed-curable composition as described above.

The photoinitiators of formula (II) in combination with compounds of formula (I) are also suitable for use as a photolatent base in photocurable systems, that is to say as generators of bases that are photochemically activated.

The invention therefore relates also to base-catalysed-curable compositions comprising
(F) at least one base-catalysed-polymerisable or polycondensable compound;
(B) at least one photoinitiator compound of formula (II) as defined in claim 4; and
(C) as storage-stability improver at least one compound of formula (I) as defined in claim 1, and
(D1) optionally a sensitiser compound (as described above).

Such formulations are described, for example, in EP 0 898 202 or WO 01/92362. Formulations suitable for such applications comprise at least one base-catalysed-polymerisable or polycondensable component. Such formulations comprise as component (F) compounds having at least two different reactive groups that are able to react in an addition or condensation reaction under base catalysis.

The two (or more) reactive groups can either be contained in one resin component or they may be present in two or more different resin components. Those components undergo crosslinking under the action of the amines released from the photoinitiators of formula (II). Examples of such applications are formulations that comprise, as constituent of component (F), polymers, oligomers or monomers that are functionalised with epoxy groups and that either comprise in the same polymers, oligomers or monomers a functional group that is able to react with the epoxide under base catalysis or comprise one or more further oligomers or monomers having such a functional group.

Compounds as constituents of component (F) having suitable functional groups that are able to react with an epoxide under base catalysis are, for example, carboxylic acids, carboxylic anhydrides, thiols, amines, amides or generally compounds containing "active" hydrogen atoms. Suitable epoxides, carboxylic acids etc. can be found, for example, in EP 898 202, p. 9 ff.

Suitable epoxy compounds are generally any compounds containing epoxy groups, monomeric or dimeric epoxides and also oligomeric or polymeric compounds having epoxy groups, e.g. epoxidised acrylates, glycidyl ethers of bisphenol A, such as 2,2-bis[4-(2,3-epoxypropoxy)phenyl]propane, phenol and cresol epoxy novolaks, glycidyl ethers of aliphatic diols, digiycidyl ethers of bisphenol A, such as 2,2-bis[4-(2,3-epoxypropoxy)cyclohexyl]-propane, 1,1,2,2-tetrakis[4-(2,3-epoxypropoxy)phenyl]ethane, triglycidyl isocyanurate, and many other compounds known to the person skilled in the art. Preference is given to compounds having at least two epoxy groups. Examples can be found in Ullmann's Encyclopedia of Industrial Chemistry, 5$^{th}$ Edition, Vol. A9, Weinheim, N.Y., pages 547-553.

Suitable as carboxylic acids are any compounds that contain at least one carboxylic acid group that is able to react with the epoxide, for example dicarboxylic acids or polymeric acids. Specific examples are malonic acid, succinic acid, glutaric acid, adipic acid, sebacic acid, phthalic acid, terephthalic acid, maleic acid, cyclohexanedicarboxylic acid, polymeric acids, e.g. partially hydrolysed polyacrylates, for example Carboset resins, such as are obtainable from Goodrich USA. It is also possible to use copolymers of unsaturated compounds with or without an acid function. Examples are partially esterified styrene/maleic anhydride copolymers, for example such as those available from Monsanto under the trade name Scripset. Copolymers that contain both epoxy and acid groups can also be used. Examples of suitable anhydrides are especially dibasic anhydrides. Specific examples are phthalic anhydride, methyltetrahydrophthalic anhydride, tetrahydrophthalic anhydride, hexahydrophthalic anhydride, methylhexahydrophthalic anhydride, succinic anhydride, maleic anhydride, itaconic anhydride. Examples are disclosed in U.S. Pat. No. 5,009,982 and JP-A 89-141904. Compounds having at least two acid groups are preferred.

Suitable thiols are monomeric, oligomeric, aliphatic or aromatic thiols. Examples are pentaerythritol tetra(mercaptoacetate), pentaerythritol tetra(mercaptopropionate), 4,4'-thiobisbenzenethiol, dithiothreitol (=threo-1,4-dimercapto-2,3-butanediol), dithioerythritol (=erythro-1,4-dimercapto-2,3-butanediol), mercaptoethanol, dodecanethiol, thioglycolic acid, 3-mercaptopropionic acid and ethylene glycol dimercaptoacetate.

Further examples can be found in EP 706 091, EP 747 770, WO 96/41240 and DE 196 22 464. U.S. Pat. No. 4,943,516 likewise gives examples of resins that can be cured with photolatent bases.

Further examples of binder systems that can be crosslinked by a base, such as photoinitiators of formula (II) that have been stabilised with compounds of formula (I), are:

1. acrylate polymers having alkoxysilane or alkoxysiloxane side groups, as described, for example, in U.S. Pat. No. 4,772,672 or U.S. Pat. No. 4,444,974;
2. two-component systems, consisting of a polyacrylate, polyester and/or polyether oligomer substituted by hydroxyl groups, and aliphatic or aromatic polyisocyanates;
3. two-component systems consisting of a polyacrylate and a polyepoxide, the polyacrylate being substituted by carboxylate, carboxylic anhydride, thiol or amino groups;
4. two-component systems consisting of fluoro- or silicone-modified polyacrylates that are substituted by hydroxyl groups, polyesters and/or polyethers containing hydroxyl groups, and aromatic or aliphatic polyisocyanates;
5. two-component systems, consisting of (poly)ketimines and aliphatic or aromatic poly-isocyanates;
6. two-component systems, consisting of (poly)ketimines and unsaturated acrylate or acetoacetate resins, or methyl-a-acrylamido-methylglycolates, two-component systems, consisting of polyacrylates that are substituted by carboxylic anhydride groups, and polyamines;
7. two-component systems, consisting of (poly)oxazolidines and polyacrylates that are substituted by carboxylic anhydride groups, or unsaturated acrylate resins or aliphatic or aromatic polyisocyanates;
8. two-component systems, consisting of polyacrylates containing epoxy groups, and polyacrylates containing carboxyl or amino groups;
9. polymers based on allyl or glycidyl ethers;
10. two-component systems, consisting of a (poly)alcohol and an aliphatic or aromatic polyisocyanate;
11. two-component systems, consisting of a (poly)thiol and an aliphatic or aromatic polyisocyanate.

A description of polythiols and polyisocyanates can be found, for example, in WO 01/92362.

It is, of course, also possible to use any combination of the components described above. It is likewise possible to use components having more than one of the mentioned functionalities, for example hydroxyl groups and thiol groups.

In the case of one-component systems, the two components first can be mixed with photoinitiators of formula (II) that have been stabilised with compounds of formula (I) and then the one-pot system can be stored in the dark until photocuring, without undesirable crosslinking taking place.

It is also possible to store the two components separately and to mix them together only shortly before processing. In that case the photoinitiators of formula (II) that have been stabilised with compounds of formula (I) can be mixed into one or more of the resin components. The use of the formulations as a two-component system has advantages especially when the two components are able to react slowly at room temperature even without a catalyst. When the formulation used is a multi-component system that is mixed together only shortly before processing, the photoinitiator of formula (II) that has been stabilised with compounds of formula (I) can also be used as a separate component, for example by dissolving it in a suitable solvent and adding the resulting solution to the formulation during mixing of the components. Suitable solvents are, for example, toluene, ortho-, meta- or para-xylene or mixtures of those isomers. Also suitable are n-butyl acetate and isobutyl acetate. The person skilled in the art will readily be able to identify further suitable solvents. The photoinitiators of formula (II) that have been stabilised with compounds of formula (I) may, if desired, be admixed with further photoinitiators that generate an amine under the action of light. Examples thereof are N-substituted 4-(ortho-nitrophenyl)-dihydropyridines, or quaternary ammonium salts of organoborates, as described e.g. in WO 00/10964.

The photolatent bases are usually used in an amount of from 0.01 to 10% by weight, preferably from 0.05 to 5% by weight, based on the resin component.

The photoinitiators of formula (II) that have been stabilised with compounds of formula (I) can, if desired, also be admixed with sensitisers in order to increase their sensitivity to light, especially of relatively long wavelengths. Suitable sensitisers include the compounds described above.

It is also possible to use combinations of the above-described formulation components with those able to enter into free-radical polymerisation. In that case it is a so-called hybrid system in which some of the crosslinking takes place by way of photoinitiated free-radical polymerisation, while another portion of the crosslinking takes place by way of one of the base-catalysed crosslinking reactions described above. Depending upon the conditions, the free-radical polymersation can be carried out before or after the base-catalysed crosslinking, or the two processes take place simultaneously.

Since photoinitiators of formula (II) that have been stabilised with compounds of formula (I) generate both free radicals and an amine, such curing processes of hybrid systems can be carried out using those photoinitiators alone. If desired, however, it is also possible for one or more free-radical photoinitiators as described above to be added in addition. It is also possible to add one or more of the photolatent amines described above. For complete reaction of the base-catalysed crosslinking process, where appropriate a thermal aftertreatment is carried out after the irradiation.

In some applications the formulation components can be used also in the form of aqueous dispersions, for example hydrophilic organic polyisocyanates having non-ionic groups, such as $C_1$-$C_4$alkoxypolyalkylene oxide groups. In such cases, the water is generally removed before the crosslinking step, e.g. by a thermal pretreatment after application of the formulation to the support material.

Full-cure is effected by irradiation with light of a wavelength from 150 nm to 600 nm. Suitable light sources are those already described above. Depending upon the application, the irradiation takes place over the entire area or imagewise, there being used in the latter case suitable tools, such as photomasks or directly controllable laser irradiation apparatus, as described above.

According to the reactivity of the formulation components used and the desired curing rate, full-cure is effected after irradiation at room temperature. In other cases it is advisable to carry out a thermal aftertreatment after irradiation in order to effect rapid and complete full-cure. The aftertreatment temperatures are in the range of from 25 to 180° C., preferably from 25 to 160° C., depending on the system.

When imagewise exposure is carried out, full-cure is generally followed by a development step, as already described above.

In some cases it is desirable to add additional basic catalysts to the formulations in addition to the photoinitiators of formula (II) that have been stabilised with compounds of formula (I). Such catalysts are, for example, imidazole derivatives, triazine derivatives or guanidine derivatives, as described e.g. in EP 0 898 202, p. 14, line 53 ff. When one of the resin components is a polyisocyanate it is also possible to add metal complexes or metal salts known as catalysts of addition reactions with isocyanates. Examples are e.g. the aluminium complex K-KAT® XC5218 (Kings Industries) or organotitanates, such as titanium diisopropoxide bis-2,4-pentadionate) (Tyzor® AA, DuPont), or tin catalysts, for example dibutyltin dilaurate or dibutyltin diacetate.

Furthermore, any formulations that are cured by a photolatent amine can, if required, be admixed with the customary additives and auxiliaries known to the person skilled in the art. These include, for example, additives such as stabilisers, light stabilisers, flow improvers, adhesion promoters, or additives such as e.g. waxes, fillers, pigments, as already described hereinabove. The addition of an acid, e.g. dodecylbenzenesulfonic acid, can further enhance the storage stability of the formulations.

The described base-catalysed-crosslinking formulations comprising photoinitiators of formula (II) that have been stabilised with compounds of formula (I) can be used, for example, in protective coatings, basecoats, priming varnishes, primers, topcoats, coating varnishes, automotive repair coatings, decorative coatings, UV-curable powder coatings, negative resists or printing plates. The formulations may be applied to any support material, for example metal, plastics, wood, glass, ceramics or to other coatings.

The invention therefore relates also to the use of a base-catalysed-curable composition in the production of pigmented and non-pigmented surface coatings, protective coatings, basecoats, priming varnishes, primers, topcoats, coating varnishes, automotive repair coatings, decorative coatings, UV-curable powder coatings, UV-curable ink-jet inks, negative resists or printing plates; and to a process for the production of pigmented and non-pigmented surface-coatings, protective coatings, basecoats, priming varnishes, primers, topcoats, coating varnishes, automotive repair coatings, decorative coatings, UV-curable powder coatings, UV-curable ink-jet inks, negative resists or printing plates by base-catalysed curing of a composition as described above.

The following Examples further illustrate the invention. In the Examples, as in the remainder of the description and in the patent claims, unless otherwise indicated parts and percentages relate to weight. Where alkyl or alkoxy radicals having more than three carbon atoms are mentioned without any reference to their isomeric form, the data relate to the respective n-isomer.

EXAMPLE 1

Preparation of 2-hydroxy-2-(4-morpholinophenyl)-1-(4-methylphenyl)-pentan-3-one

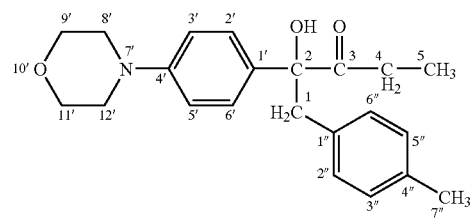

1.1: 2-(4-Morpholinophenyl)-2-trimethylsilyloxy-ethanenitrile 0.11 mol of trimethylsilyl cyanide in 50 ml of tetrahydrofuran are added dropwise to a solution of 0.1 mol 4-morpholinobenzaldehyde and 0.01 mol zinc iodide in 250 ml of dry tetrahydrofuran at 0° C. The reaction mixture is stirred overnight at room temperature. The solvent is removed and the crude product is used without further purification in the next step.

1.2: 1-Hydroxy-1-(4-morpholinophenyl)-butan-2-one

Ethyl magnesium bromide in ether is prepared by slowly adding a solution of ethyl bromide in ether to magnesium at slight reflux. When all the magnesium is dissolved, the solution is cooled to 0° C. and a solution of one equivalent of 2-(4-morpholinophenyl)2-trimethylsilyloxy-ethanenitrile (prepared according to step 1.1) is slowly added. The reaction mixture is kept at room temperature for two hours and subsequently heated to reflux for a further five hours. After cooling the reaction mixture is poured onto a mixture of 2M HCl and ice. The suspension is efficiently stirred at room temperature overnight. The organic layer is separated, the water phase extracted with dichloromethane and the combined organic extracts washed with brine and dried over magnesium sulfate. Evaporation of the solvent and chromatography on silica gel (hexane/ethyl acetate 4:1) gives 1-hydroxy-1-(4-morpholinophenyl)-butan-2-one.

1.3: 2-Hydroxy-2-(4-morpholinophenyl)-1-(4-methylphenyl)-pentan-3-one

1-Hydroxy-1-(4-morpholinophenyl)-butan-2-one, one equivalent of 4-methylphenylmethyl bromide and 1.2 equivalent of sodium hydroxide are suspended in dimethyl sulfoxide and the resulting mixture is stirred at room temperature for 24 hours. The reaction mixture is diluted with the same amount of water and extracted several times with dichloromethane. The combined organic extracts are dried over sodium sulfate and evaporated to give crude 2-hydroxy-2-(4-morpholinophenyl)-1-(4-methylphenyl)-pentan-3-one as a viscous oil. The compound is purified by chromatography on silica gel (eluant: hexane/ethyl acetate 9:1). Pure 2-hydroxy-2-(4-morpholinophenyl)-1-(4-methylphenyl)-pentan-3-one is thus obtained as colorless crystals with a melting point of 160° C.

Elemental analysis: $C_{22}H_{27}NO_3$ (MW=353.47)

|  | C % | H % | N % |
|---|---|---|---|
| Calculated: | 74.76 | 7.70 | 3.96 |
| Found: | 74.22 | 7.76 | 3.94 |

IR (cm$^{-1}$, KBr pellet): 3379 (OH), 1707 (C=O). $^1$H-NMR (300 MHz, CDCl$_3$): 7.41 (d, 2H—C(3'/5')); 7.05 (broad s, 4 H—C(2", 3", 5", 6")); 3.85 (m, 4 H—C(9'/11')); 3.58 (d, 1H—C(1)); 3.28 (d, 1H—C(1)); 3.17 (m, 4 H—C(8'/12')); 2.65-2.34 (m, 2 H—C(4)); 2.29 (s, 3 H—C(7")); 1.58 (broad s, OH); 0.98 (t, 3 H—C(5)). $^{13}$C-NMR (300 MHz, CDCl$_3$): 212 (C(3)); 150.7 (C(5')); 136.6 (C(1"); 132.3 and 132.2 (C(2") and C(6')); 130.2, 129.1, 127.0 (6 aromatic C)); 115.3 (C(3'/5'); 82.5 (C(2)); 66.9 (C(9) and C(11')); 49.0 (C(8') and C(12')); 43.0 (C(1)); 29.9 (C(4)); 21.0 (C(7")); 7.9 (C(5)).

EXAMPLE 2:

Preparation of

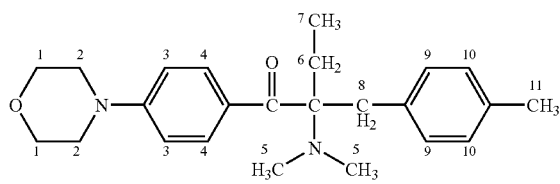

The synthesis is performed following the description in EP 805152-A, Example 25, by replacing benzyl bromide by 4-methylbenzyl bromide.

After crystallization from methanol, a crude product with a melting point of 82.5° C. is obtained as yellowish crystals. 40 g of these crystals are dissolved in 200 ml of diethyl ether and 58 ml of 10% HCl are added. After vigorous stirring, the water phase is separated and washed 5 times with 50 ml of diethyl ether. To the water phase are added 63 ml of 10% NaOH and the product is extracted with 2 portions of 50 ml of diethyl ether. The organic layer is separated, dried with sodium sulfate and evaporated to dryness. To the warm syrup are added 160 ml of methanol and the solution is cooled to room temperature with stirring. The product crystallizes as pale yellow crystals. To further purify the product, the crystallization step with methanol is repeated 2 times. This procedure yields the title product as slightly yellowish crystals melting at 85.5° C.

Analytical Data:

$^1$H NMR (ppm; with TMS=0 ppm as internal standard); 1 as t at 3.83-3.87, 2 as t at 3.27-3.31, 3 as d at 6.80+6.83, 4 as d at 8.35+8.38, 5 as s at 2.36, 6 as 2×broad m (AB-system) at 1.80-2.11, 7 as t at 0.68-0.73, 8 as s at 3.15, 9 as d at 7.11+7.13, 10 as d at 7.01+7.03, 11 as s at 2.29.

EXAMPLE 3

Storage Stability of a Solution of a Photoinitiator in a Triacrylate

The following formulations comprising a photoinitiator are prepared by mixing together the components:
photoinitiator A: 100.0% compound of Example 2
stabilised photoinitiator B: 97.5% compound of Example 2 and
2.5% compound of Example 1

24% by weight of photoinitiator A and 24% by weight of the stabilised photoinitiator B are each stirred into tripropylene glycol trisacrylate. The two solutions are stored at 5° C. in a refrigerator. After 24 hours the non-stabilised solution (photoinitiator A) contains a precipitate, while the solution comprising a compound of formula (I) (photoinitiator B) remains clear.

This Example shows that by the addition of a compound of formula (I) the storage stability of the solution comprising the photoinitiator is improved.

EXAMPLE 4

Storage Stability of a Photoinitiator

30% by weight of the photoinitiators A and B described in Example 3 are stirred into hexanediol diacrylate. The two solutions are stored at room temperature. After 3 days the non-stabilised solution (photoinitiator A) contains crystals, while the solution comprising a compound of formula (I) according to the invention (photoinitiator B) remains clear.

EXAMPLE 5

Photocuring of a White Screen-printing Ink

A photocurable formulation is prepared by mixing together the following components:

| | |
|---|---|
| 8.0 g | of an amide-modified polyester acrylate ($^{RTM}$Ebecryl 83; UCB) |
| 14.0 g | of an epoxy acrylate (EB 604) + 20% 1,6-hexanediol diacrylate (= IRR 33; UCB) |
| 4.0 g | of a fully acrylated oligomer, diluted in 40% tripropylene glycol diacrylate (Ebecryl 740; UCB) |
| 13.0 g | of trimethylolpropane triacrylate |
| 8.0 g | of 1,6-hexanediol diacrylate |
| 2.0 g | of a silicic acid ($^{RTM}$Aerosil 200; Degussa) |
| 0.5 g | of a flow agent ($^{RTM}$Modaflow; Monsanto) |
| 0.5 g | of an antifoam ($^{RTM}$Byk VP-141; Byk-Mallinckrodt) |
| 50.0 g | of titanium dioxide |
| 100.0 g | of white screen-printing ink |

The photoinitiators A and B (as described in Example 3) are each incorporated into this formulation in a concentration of 4% by weight.

The coating is applied to aluminium sheet for the reactivity test and to white cardboard for the discoloration test and then cured. Curing is effected by passing the samples on a conveyor belt moving at a defined speed under two 80 W/cm medium-pressure mercury lamps (IST, Germany). The resistance to wiping, the through-curing and the yellowing of the samples are tested. Comparable results in the range of margins of error are achieved for both formulations.

This Example shows that the addition of a compound of formula (II) to the photoinitiator does not have an adverse effect on the curing result of the formulation.

What is claimed is:

1. A compound of formula (I)

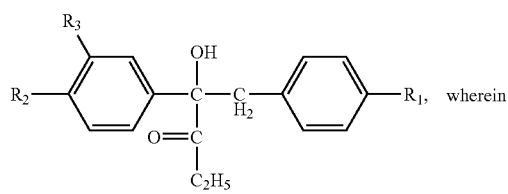

$R_1$ is hydrogen or alkyl;
$R_2$ is $C_1$-$C_4$alkoxy or a morpholino radical; and
$R_3$ is hydrogen or $C_1$-$C_4$alkoxy.

2. A compound of formula (I) according to claim 1, wherein
$R_1$ is hydrogen or $C_1$-$C_4$alkyl, especially methyl;
$R_2$ is methoxy or a morpholino radical; and
$R_3$ is hydrogen or methoxy.

3. A compound of formula (I) according to claim 1

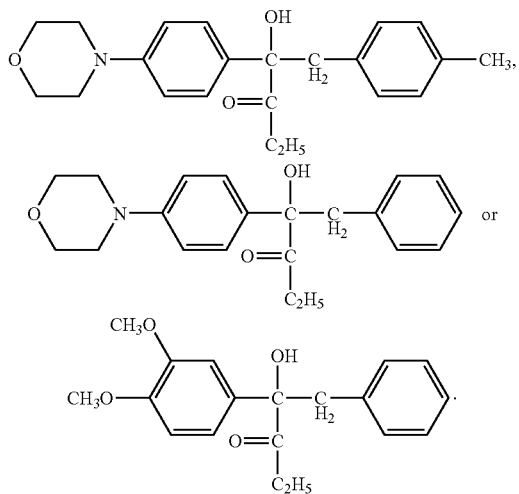

4. A mixture of a compound of formula (I), as defined in claim 1, with a compound of formula (II)

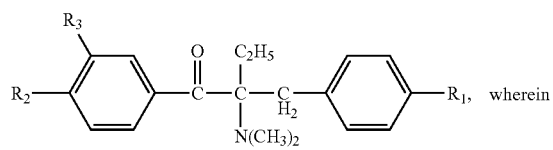

$R_1$, $R_2$ and $R_3$ are as defined in claim 1.

5. A mixture according to claim 4, containing from 0.1 to 10% of a compound of formula (I)

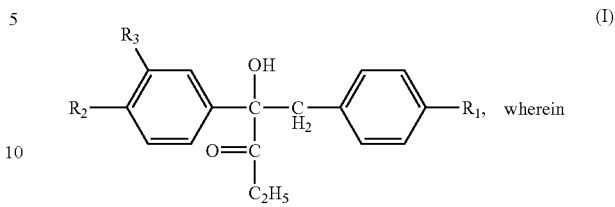

$R_1$ is hydrogen or alkyl;
$R_2$ is $C_1$-$C_4$alkoxy or a morpholino radical; and
$R_3$ is hydrogen or $C_1$-$C_4$alkoxy
and from 90 to 99.9% of a compound of formula (II).

6. A mixture of a compound of formula (I) with a compound of formula (II),

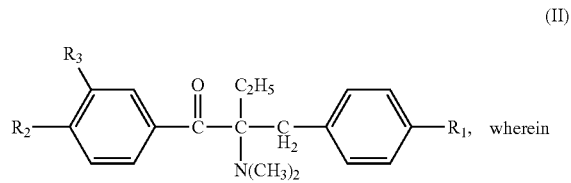

$R_1$, $R_2$ and $R_3$ are as defined in claim 1
comprising
a compound of formula (I) and a compound of formula (II) wherein in each case $R_1$ is methyl, $R_2$ is a morpholino radical and $R_3$ is hydrogen;
or comprising
a compound of formula (I) and a compound of formula (II) wherein in each case $R_1$ is hydrogen, $R_2$ is a morpholino radical and $R_3$ is hydrogen;
or comprising
a compound of formula (I) and a compound of formula (II) wherein in each case $R_1$ is hydrogen and $R_2$ and $R_3$ are methoxy.

7. A method of improving the storage stability of a formulation comprising a compound of formula (II) as defined in claim 4, wherein at least one compound of formula (I)

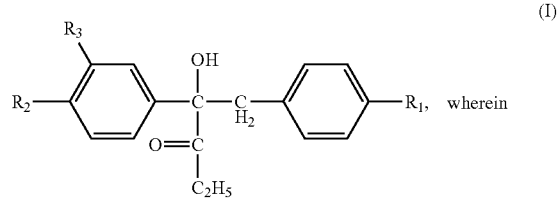

$R_1$ is hydrogen or alkyl;
$R_2$ is $C_1$-$C_4$alkoxy or a morpholino radical; and
$R_3$ is hydrogen or $C_1$-$C_4$alkoxy
is added to the formulation.

8. A photopolymerisable composition comprising
(A) at least one ethylenically unsaturated photopolymerisable compound, (B) at least one photoinitiator compound of formula (II),

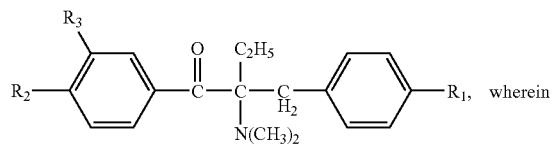

(II)

$R_1$, $R_2$ and $R_3$ are as defined in claim 1,
and
(C) as storage-stability improver at least one compound of formula (I) as defined in claim 1.

9. A composition according to claim 8, comprising, in addition to component (B), further photoinitiator(s) (E) and/or additive(s) (D).

10. A composition according to claim 8, containing from 0.05 to 20% by weight of photoinitiator component (B), or from 0.05 to 20% by weight of photoinitiator components (B)+(E), based on the composition.

11. A process for the photopolymerisation of non-volatile monomeric, oligomeric or polymeric compounds having at least one ethylenically unsaturated double bond, wherein a composition according to claim 8 is irradiated with light in a range of from 200 to 600 nm.

12. A process according to claim 11 for the production of pigmented and non-pigmented surface coatings, printing inks, screen-printing inks, offset printing inks, flexographic printing inks, UV-curable ink-jet inks, powder coatings, printing plates, adhesives, dental compounds, light waveguides, optical switches, color-testing systems, composite materials, glass fiber cable coatings, screen-printing stencils, resist materials, color filters, gel coats (fine layers), for encapsulating electrical and electronic components, for the production of magnetic recording materials, for the production of three-dimensional articles by means of stereolithography, for the production of photographic reproductions, image-recording material, for holographic recordings, for the production of decolorising materials, for the production of decolorising materials for image-recording materials, for the production of image-recording materials using microcapsules.

13. A coated substrate that has been coated on at least one surface with a composition according to claim 8.

14. A base-catalysed-curable composition comprising
(F) at least one base-catalysed-polymerisable or polycondensable compound;
(B) at least one photoinitiator compound of formula (II);

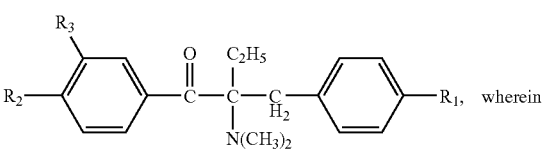

(II)

$R_1$, $R_2$ and $R_3$ are as defined in claim 1,
and
(C) as storage-stability improver at least one compound of formula (I) as defined in claim 1, and
(D1) optionally a sensitiser compound.

15. A process for the production of pigmented and non-pigmented surface coatings, protective coatings, basecoats, priming varnishes, primers, topcoats, coating varnishes, automotive repair coatings, decorative coatings, UV-curable powder coatings, UV-curable ink-jet inks, negative resists or printing plates by base-catalysed curing of a compositon according to claim 14.

* * * * *